US009622884B2

(12) United States Patent
Holgate et al.

(10) Patent No.: US 9,622,884 B2
(45) Date of Patent: Apr. 18, 2017

(54) CONTROL SYSTEMS AND METHODS FOR GAIT DEVICES

(71) Applicant: SpringActive, Inc., Tempe, AZ (US)

(72) Inventors: Matthew A. Holgate, Chandler, AZ (US); Nathan Cahill, Tempe, AZ (US)

(73) Assignee: SpringActive, Inc., Tempe, AZ (US)

(*) Notice: Subject to any disclaimer, the term of this patent is extended or adjusted under 35 U.S.C. 154(b) by 0 days.

(21) Appl. No.: 14/210,331

(22) Filed: Mar. 13, 2014

(65) Prior Publication Data
US 2014/0200680 A1    Jul. 17, 2014

Related U.S. Application Data

(63) Continuation-in-part of application No. 13/767,945, filed on Feb. 15, 2013.
(Continued)

(51) Int. Cl.
*A61F 2/70* (2006.01)
*A61F 2/66* (2006.01)
(Continued)

(52) U.S. Cl.
CPC ............... *A61F 2/66* (2013.01); *A61F 2/60* (2013.01); *A61F 2/68* (2013.01); *A61F 5/02* (2013.01);
(Continued)

(58) Field of Classification Search
CPC ........................................................ A61F 2/72
(Continued)

(56) References Cited

U.S. PATENT DOCUMENTS 7,112,938 B2   9/2006   Takenaka et al.
7,300,240 B2   11/2007   Brogardh
(Continued)

FOREIGN PATENT DOCUMENTS

WO   2011005482 A2   1/2011
WO   2011096965 A2   8/2011
WO   2013086035 A1   6/2013

OTHER PUBLICATIONS

Hitt J. et al., "An Active Foot-Ankle Prosthesis with Biomechanical Energy Regeneration", Journal of Medical Devices, vol. 4, 2010.
(Continued)

*Primary Examiner* — Jacqueline Woznicki
(74) *Attorney, Agent, or Firm* — Robert D. Atkins; Atkins and Associates, P.C.

(57) ABSTRACT

A method of controlling a gait device includes a first sensor disposed on a first mobile body. A physical state of the first mobile body is measured using the first sensor to obtain a first physical state measurement. A second sensor is disposed on a second mobile body. A physical state of the second mobile body is measured using the second sensor to obtain a second physical state measurement. The first and second physical state measurements are conditioned by pseudo integration. A reference function is based on a gait activity. A reference function is determined by measuring a physical state of an able-bodied human and correlating an output position of the actuator to the physical state of the able-bodied human. A command is generated by inputting the first and second physical state measurements into the reference function to control an actuator of the gait device to match the output position.

25 Claims, 26 Drawing Sheets

Related U.S. Application Data

(60) Provisional application No. 61/600,141, filed on Feb. 17, 2012, provisional application No. 61/790,259, filed on Mar. 15, 2013.

(51) Int. Cl.
   | | |
   |---|---|
   | *A61F 2/68* | (2006.01) |
   | *A61F 2/60* | (2006.01) |
   | *A61F 5/02* | (2006.01) |
   | *A61F 2/72* | (2006.01) |
   | *A61F 2/76* | (2006.01) |

(52) U.S. Cl.
   CPC ........... *A61F 2/72* (2013.01); *A61F 2002/704* (2013.01); *A61F 2002/762* (2013.01); *A61F 2002/764* (2013.01); *A61F 2002/7625* (2013.01); *A61F 2002/7635* (2013.01); *A61F 2002/7645* (2013.01)

(58) Field of Classification Search
   USPC .......................................................... 623/25
   See application file for complete search history.

(56) References Cited

U.S. PATENT DOCUMENTS

| | | | |
|---|---|---|---|
| 7,431,737 | B2 | 10/2008 | Ragnarsdottir et al. |
| 7,811,333 | B2 | 10/2010 | Jonsson et al. |
| 7,896,927 | B2 | 3/2011 | Clausen et al. |
| 8,057,550 | B2 | 11/2011 | Clausen et al. |
| 8,287,477 | B1 | 10/2012 | Herr et al. |
| 8,419,804 | B2 | 4/2013 | Herr et al. |
| 8,551,184 | B1 | 10/2013 | Herr |
| 8,601,897 | B2 | 12/2013 | Lauzier et al. |
| 8,716,877 | B2 | 5/2014 | Sugar et al. |
| 8,734,528 | B2 | 5/2014 | Herr et al. |
| 2002/0007690 | A1 | 1/2002 | Song et al. |
| 2005/0070834 | A1 | 3/2005 | Herr et al. |
| 2006/0046907 | A1 | 3/2006 | Rastegar et al. |
| 2006/0122710 | A1* | 6/2006 | Bedard .................... A61F 2/644 623/24 |
| 2006/0173552 | A1* | 8/2006 | Roy .............................. 623/24 |
| 2006/0189899 | A1* | 8/2006 | Flaherty et al. .............. 600/595 |
| 2007/0129653 | A1 | 6/2007 | Sugar et al. |
| 2008/0058668 | A1* | 3/2008 | Seyed Momen et al. .... 600/546 |
| 2009/0088912 | A1 | 4/2009 | Rajaraman |
| 2010/0161077 | A1 | 6/2010 | Boone et al. |
| 2010/0275718 | A1 | 11/2010 | Stuart et al. |
| 2011/0126660 | A1 | 6/2011 | Lauzier et al. |
| 2011/0132131 | A1 | 6/2011 | Worz |
| 2012/0078415 | A1 | 3/2012 | Kubo et al. |
| 2014/0114437 | A1 | 4/2014 | Herr et al. |
| 2014/0121782 | A1 | 5/2014 | Herr et al. |
| 2015/0127118 | A1 | 5/2015 | Herr et al. |

OTHER PUBLICATIONS

Belforte G. et. al., "Pneumatic Active Gait Orthosis". Mechatronics 11, 2001, pp. 301-323.

Colombo Gery et. al., "Treadmill Training of Paraplegic Patients Using a Robotic Orthosis", Journal of Rehabilitation Research and Development. vol. 37 No. 6., 2000, pp. 693-700.

Holgate M. et al., "A Control Algorithm for a Prosthetic Ankle Using Phase Plane Invariants", Poster presentation at Dynamic Walking, Vancouver, Canada, 2009.

Guiraud D., "Application of an Artificial Neural Network to the Control of an Active External Orthosis of the Lower Limb", Medical & Biological Engineering & Computing, Nov. 1994, vol. 32, pp. 610-614.

Herr H. et al., "Patient-Adaptive Prosthetic and Orthotic Leg Systems", Proceedings of the International Federation for Medical & Biological Engineering, Reykjavik, Iceland, Jun. 18-22, 2002, pp. 18-21.

Hitt J. et al., "A Robotic Transtibial Prosthesis with Regenerative Kinetics: The Design Analyses, Methods, and Testing", U.S. Army Military Amputee Research Program, 2008.

Holgate M. et al., "Control Algorithms for Ankle Robots: a Reflection on the State-of-the-Art and Presentation of Two Novel Algorithms", 2nd IEEE RAS & EMBS International Conference on Biomedical Robotics and Biomechatronics, pp. 97-103, 2008.

Holgate M., "Control of a Robotic Transtibial Prosthesis", A Dissertation, Arizona State University, Dec. 2009.

Holgate M. et al., "A Novel Control Algorithm for Wearable Robotics Using Phase Plane Invariants", International Conference on Robotics and Automation, 2009.

Hitt J. et al., "Robotic Transtibial Prosthesis with Biomechanical Energy Regeneration", Industrial Robot: An International Journal, vol. 36, Issue 5, pp. 441-447, 2009.

Bellman R. et al., "SPARKy 3: Design of an Active Robotic Ankle Prosthesis with two Actuated Degrees of Freedom Using Regenerative Kinetics", 2nd IEEE RAS & EMBS International Conference on Biomedical Robotics and Biomechatronics, pp. 511-516, 2008.

Holgate M., "The SPARKy (Spring Ankle with Regenerative Kinetics) Project: Choosing a DC Motor Based Actuation Method" 2nd IEEE RAS & EMBS International Conference on Biomedical Robotics and Biomechatronics, pp. 163-168, 2008.

Hitt J. et al., "The SPARKy (Spring Ankle with Regenerative Kinetics) Project: Design and Analysis of a Robotic Transtibial Prosthesis with Regenerative Kinetics", ASME International Design Engineering Technical Conferences & Computers and Information in Engineering Conference (IDETC/CIE), CD-ROM, pp. 1-10, 2007.

Au S. et al. "Powered ankle-foot prosthesis to assist level-ground and stair-descent gaits," Neural Networks, 21, 2008, pp. 654-666.

Au S., "Powered Ankle-Foot Prosthesis for the Improvement of Amputee Walking Economy," Massachusetts Institute of Technology, 2007, pp. 1-108.

Hollander K. et al. "A Robust Control Concept for Robotic Ankle Gail Assistance," IEEE International Conference on Rehabilitation Robotics (ICORR), 2007, pp. 119-123.

Farley C. et al., "Biomechanics of Walking and Running: Center of Mass Movements to Muscle Action," Exerc Sport Sci Rev, vol. 26, pp. 253-285, 1998.

Au S. et al, "Powered ankle-foot prosthesis," Robotics & Automation Magazine, IEEE, vol. 15, pp. 52-59, 2008.

Au S. et al., "Powered Ankle-Foot Prosthesis for the Improvement of Amputee Ambulation," in Engineering in Medicine and Biology Society, 2007. EMBS 2007. 29th Annual International Conference of the IEEE, 2007, p. 3020.

Au S. et al., "Biomechanical Design of a Powered Ankle-Foot Prosthesis," in Rehabilitation Robotics, 2007. ICORR 2007. IEEE 10th International Conference on, 2007, pp. 298-303.

Au S. et al., "Powered Ankle-Foot Prosthesis Improves Walking Metabolic Economy," Robotics, IEEE Transactions on, vol. 25, pp. 51-66, 2009.

Sup F. et al., "Design and control of an active electrical knee and ankle prosthesis," in Biomedical Robotics and Biomechanics, 2008. BioRob 2008. 2nd IEEE RAS & EMBS International Conference on, 2008, pp. 523-528.

Kyriakopoulos K. et al., "Minimum jerk path generation." International Conference on Robotics and Automation, 1:364-369, 1988.

Hansen A. et al., "The human ankle during walking: implications for design of biomimetic ankle prostheses and orthoses," Journal of Biomechanics, 37(10): 1467-1474, 2004.

Hansen A. et al., "Prosthetic ankle-foot mechanism capable of automatic adaptation to the walking surface," J Biomech Eng-T ASME, 131(3): 035002, 2009.

Hansen A. et al., "The Effects of Prosthetic Foot Roll-over Shape Arc Length on the Gait of Trans-tibial Prosthesis Users," Prosthetics and Orthotics International, vol. 30, No. 3, 286-299, 2006.

Bernardi, M. et al., (1995), "The Efficiency of Walking of Paraplegic Patients Using a Reciprocating Gait Orthosis," Spinal Cord 33(7): 409-415.

(56) References Cited

OTHER PUBLICATIONS

Boehler, Alexander W. et al., (2008), "Design, Implementation and Test Results of a Robust Control Algorithm for a Powered Ankle Foot Orthosis," IEEE International Conference on Robotics and Automation (ICRA), IEEE.

Hitt, Joseph et al., (2010), "Dismounted Soldier Biomechanical Power Regeneration Kit (SPaRK)," Proceedings of the 27th Army Science Conference, Orlando, FL.

Hitt, Joseph et al., (2010), "Bionic Running for Unilateral Transtibial Military Amputees," Proceedings of the 27th Army Science Conference, Orlando, FL.

Hollander, Kevin W. et al., (2005), "A Robotic "Jack Spring" for Ankle Gait Assistance," DETC2005-84492, ASME International Design Engineering Technical Conference (IDETC2005), Long Beach, CA, American Society of.Mechanical Engineers.

Hollander, Kevin W. et al., (2006), "An Efficient Robotic Tendon for Gait Assistance," Journal of biomechanical engineering 128: 788.

Kawamoto, Hiroaki et al., (2003), "Power Assist Method for HAL-3 Estimating Operator's Intention Based on Motion Information," IEEE International Workshop on Robot and Human Interactive Communication, Millbrae, CA.

Kazerooni, H. et al., (2005), "On the Control of the Berkeley Lower Extremity Exoskeleton (BLEEX)," Proceedings of the 2005 IEEE International Conference on Robotics and Automation, Barcelona, Spain, Apr. 2005.

Norris, James A. et al., (2007), "Effect of Augmented Plantarflexion Power on Preferred Walking Speed and Economy in Young and Older Adults," Gait & Posture 25(4): 620-627.

Sawicki, Gregory S. et al., (2009), "Mechanics and Energetics of Incline Walking with Robotic Ankle Exoskeletons," Journal of Experimental Biology 212(1).

Sawicki, Gregory S. et al., (2009), "Powered Ankle Exoskeletons Reveal the Metabolic Cost of Plantar Flexor Mechanical Work During Walking with Longer Steps at Constant Step Frequency," Journal of Experimental Biology 212(1).

Sawicki, Gregory S. et al., (2009), "It Pays to Have a Spring in your Step," Exercise and Sport Sciences Reviews 37 (3).

Sugar, Thomas G., (2002), "A Novel Selective Compliant Actuator," Mechatronics 12(9-10): 1157-1171.

Walsh, Conor James et al., "Development of a Lightweight, Under-Actuated Exoskeleton for Load-Carrying Augmentation," Proceedings of the 2006 IEEE International Conference on Robotics and Automation, Orlando, Florida, May 2006.

Walsh, Conor James et al., (2006), Biomimetic Design of an Under-Actuated Leg Exoskeleton for Load-Carrying Augmentation, Cambridge, MA, Massachusetts Inst of Tech, M.S.

Ward, Jeffrey et al., (2007), "Robotic Gait Trainer Reliability and Stroke Patient Case Study," IEEE 10th International Conference on Rehabilitation Robotics (ICORR), Holland.

Ward, Jeffrey et al., (2008), "Control Architectures for a Powered Ankle Foot Orthsosis," International Journal of Assistive Robotics and Mechatronics 9(2): 2-13.

Ward, Jeffrey et al., (2010), "Stroke Survivor Gait Adaptation and Performance After Training on a Powered Ankle Foot Orthosis," Proceedings of the IEEE International Conference on Robotics and Automation (ICRA), Anchorage, AK, IEEE.

Ward Jeffrey et al., (2011), "Using the Translational Potential Energy of Springs for Prosthetic Systems," IEEE Multi-conference on Systems and Control, Denver, CO, IEEE.

Bellman R. et al., "SPARKy 3: Design of an Active Robotic Ankle Prosthesis with two Actuated Degrees of Freedom.Using Regenerative Kinetics", 2nd IEEE RAS & EMBS International Conference on Biomedical Robotics and Biomechatronics, pp. 511-516, 2008.

Sup F. et al., "Design and control of an active electrical knee and ankle prosthesis," in Biomedical Robotics and Biomechatronics, 2008. BioRob 2008. 2nd IEEE RAS & EMBS International Conference on, 2008, pp. 523-528.

\* cited by examiner

CONTROL SYSTEMS AND METHODS FOR GAIT DEVICES

CLAIM TO DOMESTIC PRIORITY

The present application is a continuation-in-part of U.S. application Ser. No. 13/767,945, filed Feb. 15, 2013, which claims the benefit of U.S. Provisional Application No. 61/600,141, filed Feb. 17, 2012, which applications are incorporated herein by reference. The present application further claims the benefit of U.S. Provisional Application No. 61/790,259, filed Mar. 15, 2013, which application is incorporated herein by reference.

FIELD OF THE INVENTION

The present invention relates in general to control systems and methods for gait devices, and more particularly, to control systems and methods for prosthetic, orthotic, and robotic gait devices.

BACKGROUND OF THE INVENTION

Human locomotion, such as walking and running, is commonly described in terms of gait. Gait is a cyclical pattern of leg and foot movement that creates locomotion. A gait cycle is defined for a single leg and begins with the initial contact of the foot with the ground or heel strike. The conclusion of a gait cycle occurs when the same foot makes a second heel strike. The gait cycle can be divided into two phases, stance phase and swing phase. Stance phase begins with heel strike and ends when the toe of the same foot leaves the ground. Swing phase begins when the foot leaves contact with the ground and ends with the heel strike of the same foot.

Prosthetic and orthotic devices help restore mobility to people who lack able-bodied motion or gait. Prosthetic devices are intended to replace the function or appearance of a missing limb and can return mobility to the wearer or user. Orthotic devices are intended to support or supplement an existing limb, by assisting with movement, reducing weight-bearing loads on the body, reducing pain, and controlling or restricting movement. Prosthetic and orthotic devices are available to replace or support various portions of the body. Lower limb prosthetic devices include, for example, the prosthetic foot, the foot-ankle prosthesis, the prosthetic knee joint, and the prosthetic hip joint. Lower limb orthotic devices include, for example, the foot orthoses, the ankle-foot orthoses, the knee-ankle-foot orthoses, and the knee orthoses. People who require a lower limb prosthesis or orthosis often expend more metabolic power to walk or move at the same speed as able-bodied individuals. One goal of lower limb prosthetic and orthotic devices is to help the user achieve a normal gait while reducing energy expended by the user.

Prosthetic and orthotic devices can be divided into two groups, passive devices and active devices. Passive lower limb prosthetics generally rely on compliant members, such as springs, to store and release energy. A spring is able to return only as much energy as is put into the spring. Thus, the energy that is released by a spring in a passive device is limited to the energy that is put in by the user. For example, a spring-based passive foot prosthetic provides about half of the peak power required for gait. The user of a passive device must expend additional energy through other muscles and joints to maintain a normal walking gait. Therefore, passive prosthetic and orthotic designs are limited in capacity to help users reduce metabolic energy expenditure while achieving a normal walking gait and performing other activities.

Active devices differ from passive devices in that active devices use a motor to supply power to the device and to control the device. Control systems for active devices are limited in capability to control active devices during gait or other activities. Further, active prosthetics are limited to low power activities, because the power necessary for high power activities is unattainable in a small portable system. One goal of active device designs is to increase efficiency of the active components and to build a lighter weight device.

Control systems and methods designed for prosthetic, orthotic, and robotic gait devices to control motors for active devices. One current control algorithms for wearable robotic devices use a fixed pattern designed for a specific gait pattern, such as a specific walking speed. The fixed pattern algorithms must be modified for different gait patterns or activities. Therefore, a fixed pattern algorithm is limited to a single gait speed, while a user desires to walk or run at varying speeds. Other current control algorithms for wearable robotic devices use if-then logic, estimations of gait events, or decision making algorithms to determine the phase of a user's gait cycle. Decision making and state transition algorithms are known to be error prone, often resulting in undesirable operation when a state or phase of gait is chosen incorrectly.

SUMMARY OF THE INVENTION

A need exists for control systems and methods that process user signals quickly and accurately, while providing smooth and continuous control of associated gait devices. Accordingly, in one embodiment, the present invention is a method of controlling a gait device comprising the steps of providing a first sensor disposed on a first mobile body, measuring a physical state of the first mobile body using the first sensor to obtain a first physical state measurement, providing a second sensor disposed on a second mobile body, measuring a physical state of the second mobile body using the second sensor to obtain a second physical state measurement, conditioning the first and second physical state measurements, providing a reference function based on a gait activity, and generating a command by inputting the first and second physical state measurements into the reference function to control an actuator of the gait device.

In another embodiment, the present invention is a method of controlling a gait device comprising the steps of providing a sensor, measuring a physical state of a mobile body using the sensor to obtain a physical state measurement, conditioning the physical state measurement, providing a reference function based on more than one gait activity, and generating a command by inputting the physical state measurement into the reference function to control an actuator of the gait device.

In another embodiment, the present invention is a method of controlling a gait device comprising the steps of measuring a physical state of a mobile body to obtain a physical state measurement, conditioning the physical state measurement, providing a reference function based on a gait activity, and generating a command by inputting the physical state measurement into the reference function to control an actuator of the gait device.

In another embodiment, the present invention is a gait device comprising a prosthetic limb device including an actuator. A sensor is coupled to the prosthetic limb device. A control system is coupled to the prosthetic limb device.

The control system is configured to obtain a physical state measurement from the sensor and produce a command based on a gait activity to control the actuator.

DETAILED DESCRIPTION OF THE DRAWINGS

The present invention is described in one or more embodiments in the following description with reference to the figures, in which like numerals represent the same or similar elements. While the invention is described in terms of the best mode for achieving the invention's objectives, those skilled in the art will appreciate that the description is intended to cover alternatives, modifications, and equivalents as may be included within the spirit and scope of the invention as defined by the appended claims and their equivalents as supported by the following disclosure and drawings.

Figure 1:
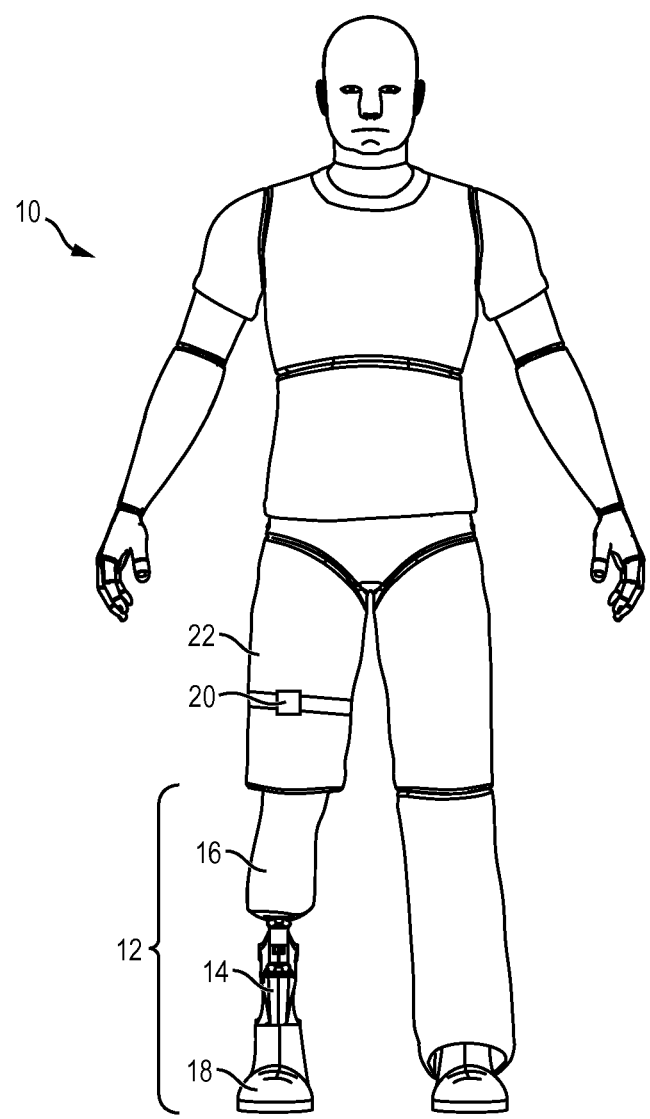
FIG. 1 illustrates a user wearing an active lower limb prosthesis with a control system.

FIG. 1 shows an example of user 10 wearing an active lower limb prosthesis 12, which includes a control system for controlling the operation of the prosthesis. Lower limb prosthesis 12 is an active prosthetic device or wearable robotic device including active and passive components. In one embodiment, lower limb prosthesis 12 is a below-the-knee prosthesis, which is also commonly known as a foot-ankle prosthesis. In another embodiment, lower limb prosthesis 12 includes a robotic or prosthetic joint, such as an ankle joint, knee joint, or other joint.

Lower limb prosthesis 12 includes an ankle prosthesis 14, a shank portion 16, and a foot portion 18. Ankle prosthesis 14 includes active components, such as one or more actuators, controlled by a computerized control system or controller. Lower limb prosthesis 12 implements a controller and an actuator to facilitate movement of lower limb prosthesis 12. A sensor or sensor system 20 is worn by user 10. In one embodiment, sensor 20 is worn on thigh 22 of user 10. In another embodiment, sensor 20 is disposed on ankle prosthesis 14, shank portion 16, foot portion 18, or other part of user 10. In yet another embodiment, a plurality of sensors 20 is disposed on user 10. Sensor 20 detects a kinematic state, a loading state, or a kinematic state and a loading state of user 10. Measurements from sensor 20 are used by the control system to control an active portion of ankle prosthesis 14 and lower limb prosthesis 12.

Figure 2:
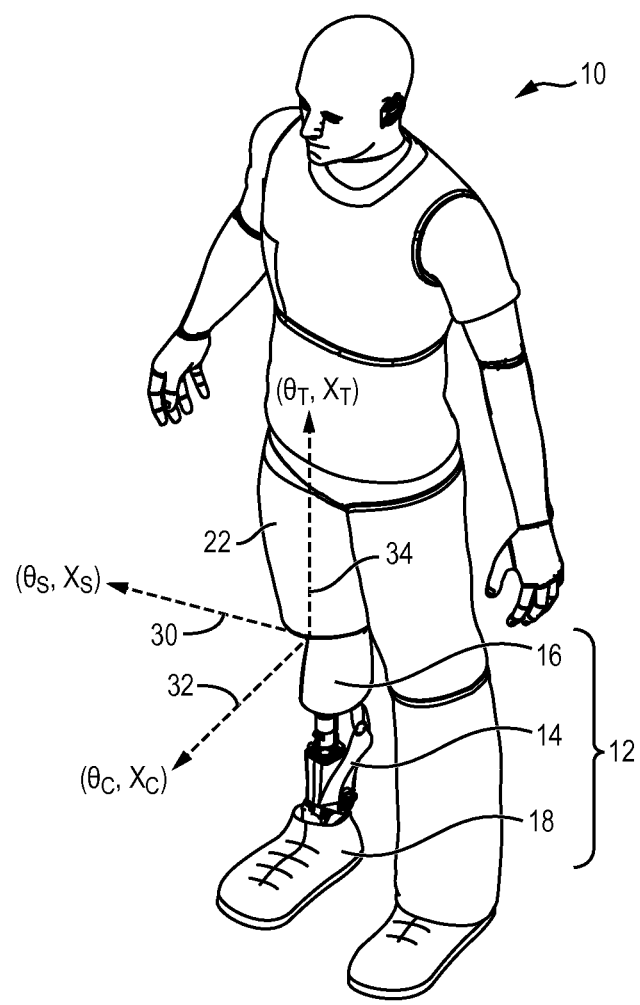
FIG. 2 illustrates a perspective view of a user shown in FIG. 1, showing a coordinate system used for controlling gait devices.

FIG. 2 shows a perspective view of user 10 shown in FIG. 1, showing a coordinate system used for controlling gait devices. Sensor 20 measures a kinematic state or loading state of a mobile body of user 10. A mobile body includes a limb segment or a robotic segment. A kinematic state includes an angular position, linear position, linear velocity, angular velocity, linear acceleration, or angular acceleration associated with a mobile body with reference to a fixed world frame or a frame fixed to any other mobile body. A loading state includes a moment or force experienced by the mobile body.

Sensors 20 are configured to measure kinematic state, such as velocities, accelerations, angular positions, and linear positions in coordinate frames, which are oriented with the limb segment or robotic segment to which sensors 20 are affixed. A limb segment includes, for example, a thigh 22 of user 10. A robotic segment includes, for example, ankle prosthesis 14, shank portion 16, or foot portion 18 of lower limb prosthesis 12. Sensor 20 determines the kinematic state of user 10 in linear coordinates, polar coordinates, or a combination of coordinate systems. The coordinate frames have three orthogonal axes: a sagittal axis ($\theta_S$, $X_S$), a coronal axis ($\theta_C$, $X_C$), and a transverse axis ($\theta_T$, $X_T$). The sagittal axis ($\theta_S$, $X_S$) is oriented normal to the sagittal plane of the mobile body, while the coronal axis ($\theta_C$, $X_C$) is oriented normal to the coronal plane of the mobile body, and the transverse axis ($\theta_T$, $X_T$) is oriented normal to the transverse plane of the mobile body. Each sensor 20 is oriented so that the axis of measurement is any linear combination of three unit vectors in the direction of the sagittal axis ($\theta_S$, $X_S$), coronal axis ($\theta_C$, $X_C$), and transverse axis ($\theta_T$, $X_T$). The sagittal direction 30, as used herein, is in the direction of sagittal axis ($\theta_S$, $X_S$) normal to the sagittal plane of the mobile body. The coronal direction 32, as used herein, is in the direction of coronal axis ($\theta_C$, $X_C$) normal to the coronal plane of the mobile body. The transverse direction 34, as used herein, is in the direction of transverse axis ($\theta_T$, $X_T$) normal to the transverse plane of the mobile body.

Figure 3:
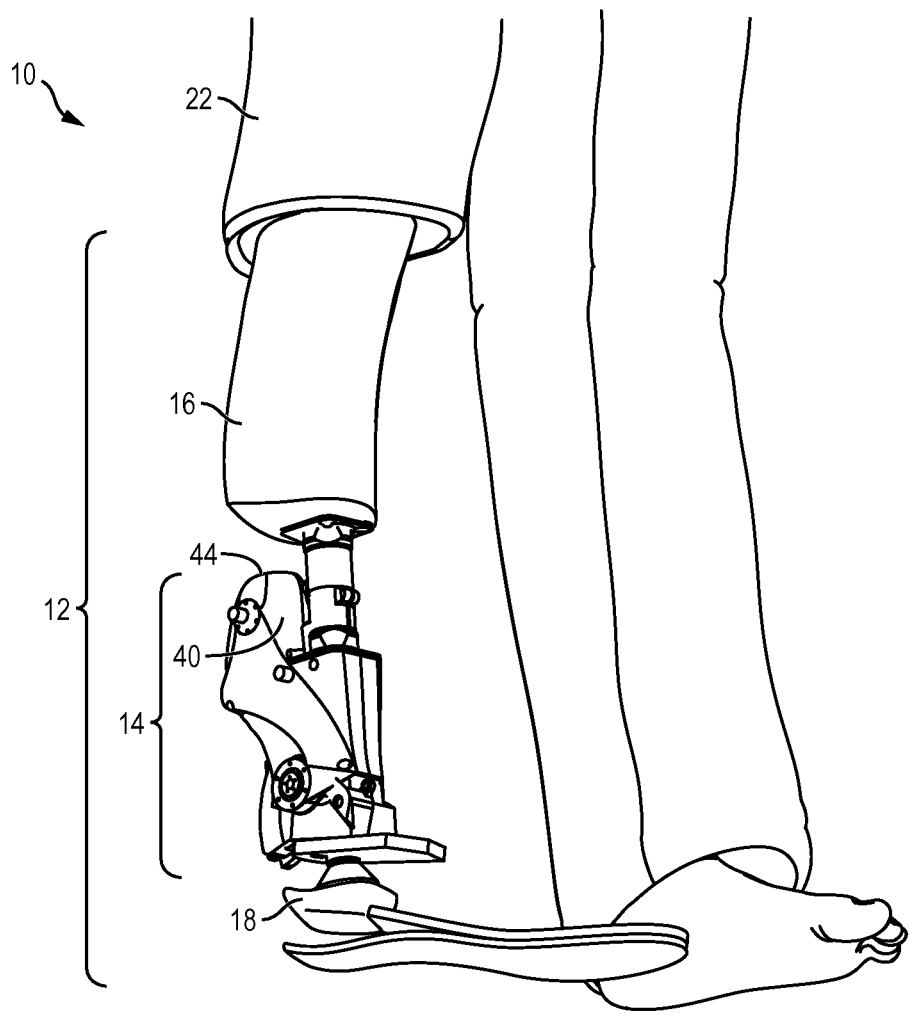
FIG. 3 illustrates an active lower limb prosthesis with a control system.

FIG. 3 shows lower limb prosthesis 12 in more detail. Lower limb prosthesis 12 is shown including ankle prosthesis 14, shank portion 16, and foot portion 18. Shank portion 16 of lower limb prosthesis 12 includes a socket or couples to a socket, which fits onto a residual limb of user 10. Ankle prosthesis 14 couples to shank portion 16, and foot portion 18 couples to ankle prosthesis 14. Ankle prosthesis 14 includes one or more active members or actuators 40, such as a motor, and may include one or more compliant members 42, such as a spring, disposed within housing 44 of ankle prosthesis 14. A control system or controller 50 is coupled to actuator 40. Control system 50 is disposed within housing 44 of ankle prosthesis 14. Control system 50 relates an input from sensor 20 and outputs a command to actuator 40 in order to control the movement of ankle prosthesis 14.

Figure 4:
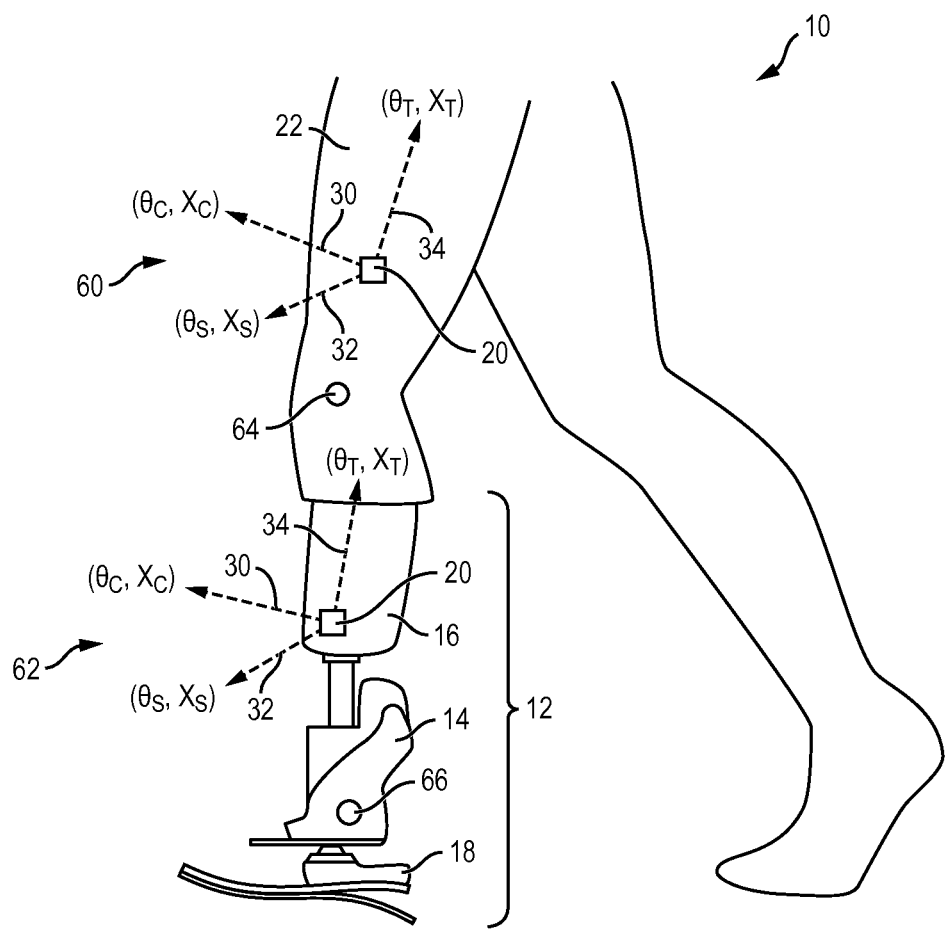
FIG. 4 illustrates a schematic representation an active lower limb prosthesis, showing an example of coordinate systems of kinematic states.

FIG. 4 shows a schematic representation of lower limb prosthesis 12 and an example of coordinate systems of kinematic states. The kinematic state or loading state of user 10 is measured using any type of sensor 20, plurality of sensors 20, or sensor system coupled to one or more limb segments 60, robotic segments 62, limb joint 64, robotic joint 66, or any type of limb-robot interface. Sensors 20 are coupled to limb segments of user 10, such as thigh 22, or are coupled to robotic segments, such as ankle prosthesis 14, shank portion 16, and foot portion 18. Sensors 20 can also be coupled to another limb or joint of user 10. In one embodiment, sensor 20 is disposed on thigh 22 of user 10 and measures a kinematic or loading state of the mobile body, which is thigh 22. In another embodiment, sensor 20 is disposed on shank portion 16 of lower limb prosthesis 12 and measures a kinematic or loading state of the mobile body, which is shank portion 16. In an alternative embodiment, sensors 20 are disposed on both a limb segment and a robotic segment of user 10 and measure a kinematic or loading state of the mobile bodies, which are the limb and robotic segments.

Sensor 20 includes an accelerometer, vibrometer, rate gyro, potentiometer, inclinometer, or other sensor. To determine a kinematic state of the mobile body, sensor 20 measures velocity, acceleration, angular position, linear position, or a combination thereof. In one embodiment, sensor 20 determines velocity, acceleration, angular position, or linear position of thigh 22 with respect to the sagittal axis ($\theta_S$, $X_S$), coronal axis ($\theta_C$, $X_C$), and transverse axis ($\theta_T$, $X_T$). In another embodiment, sensor 20 determines velocity, acceleration, angular position, or linear position of shank portion 16 with respect to the sagittal axis ($\theta_S$, $X_S$), coronal axis ($\theta_C$, $X_C$), and transverse axis ($\theta_T$, $X_T$). To determine a loading state of the mobile body, sensor 20 measures a force or moment experienced by the mobile body at one or more limb segments 60, robotic segments 62, limb joint 64, robotic joint 66, or any type of limb-robot interface. Sensor 20 determines a force or moment experienced by the mobile body with respect to the sagittal axis ($\theta_S$, $X_S$), coronal axis ($\theta_C$, $X_C$), and transverse axis ($\theta_T$, $X_T$). In one embodiment, sensor 20 is oriented such that axis of measurement is any linear combination of the three unit vectors in the direction of sagittal axis ($\theta_S$, $X_S$), coronal axis ($\theta_C$, $X_C$), and transverse axis ($\theta_T$, $X_T$). The kinematic or loading state measurements from sensors 20 are used as inputs for control system 50. Measurements from sensors 20 are ultimately used to control an actuator of ankle prosthesis 14, lower limb prosthesis 12, or other wearable robotic device.

Figure 5:
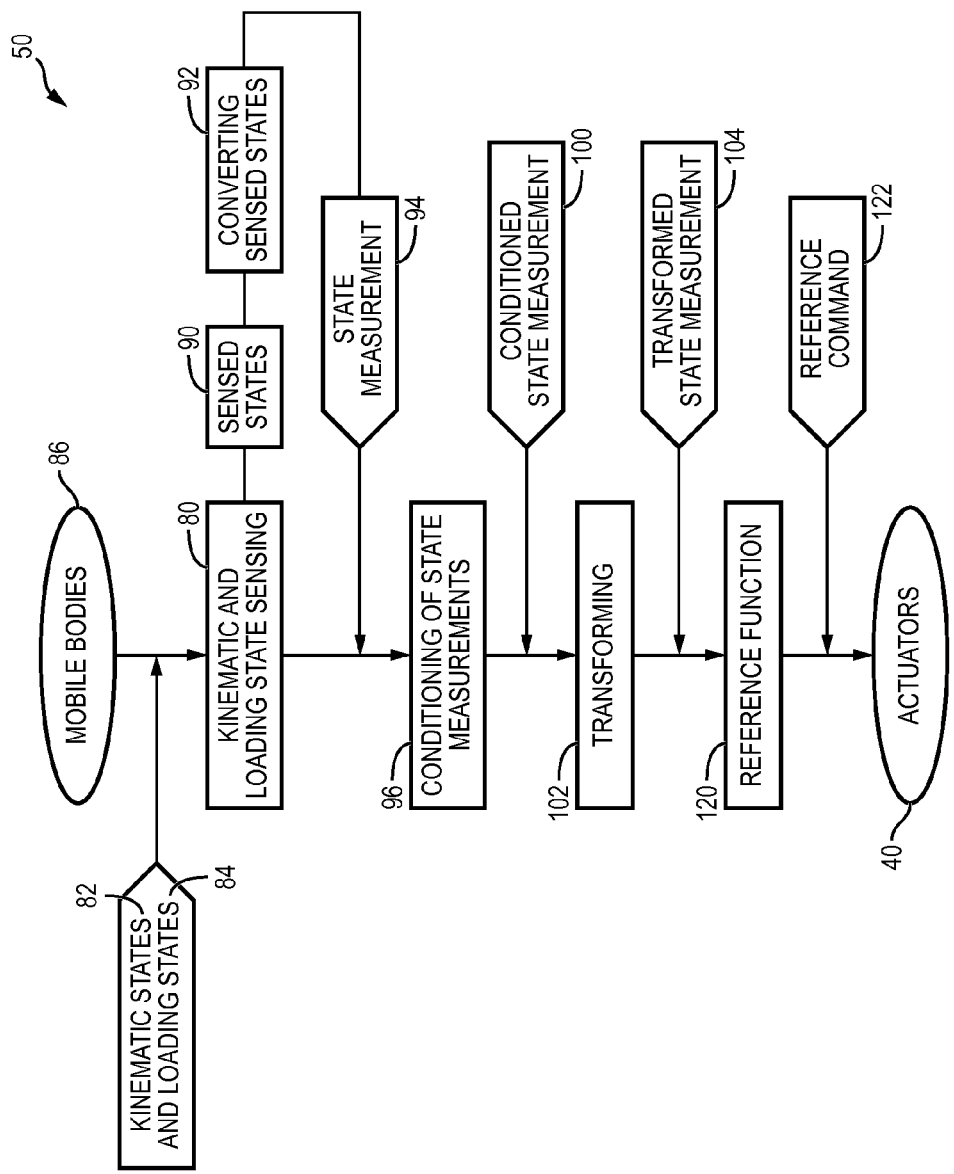
FIG. 5 illustrates a block diagram of a method for controlling gait devices using a control system.

FIG. 5 shows a block diagram of a method for controlling gait devices, such as lower limb prosthetic 12, using control system 50. Control system 50 processes data from sensor 20 to produce an output signal used to control actuator 40. Control system 50 includes a processor to store and process data from sensor 20. The method for controlling gait devices includes a series of operations performed on kinematic or loading data. The operations performed by control system 50 relate kinematic motion to a desired output of actuator 40.

The method for controlling gait devices using control system 50 includes the steps of sensing 80 kinematic states 82 and or loading states 84 generated by mobile bodies 86, converting 92 sensed states 90 into state measurements 94, conditioning 96 state measurements 94 to yield conditioned state measurements 100, transforming 102 conditioned state measurements 100 into transformed state measurements 104, and inputting transformed state measurements 104 into a reference function 120 to derive a reference command 122.

During sensing 80, sensor 20 detects or measures one or more kinematic states 82, loading states 84, or both kinematic states 82 and loading states 84 of one or more mobile bodies 86. Kinematic state 82 and loading state 84 comprise physical states of mobile body 86. After being sensed by sensor 20, kinematic state 82 and loading state 84 comprise sensed states 90. The sensed state or sensed states 90 of mobile body 86 are processed by control system 50. After sensing kinematic states 82 or loading states 84 by sensors or sensor system 20, converting 92 of sensed states 90 is performed by control system 50. Sensed states 90 are converted from an output of sensor 20 to a desired unit of measurement that yields a state measurement 94. In one embodiment, the step of converting 92 is performed by a processor of control system 50.

State measurements 94 are then conditioned using control system 50 to yield conditioned state measurements 100. Conditioning 96 is realized by any filtering method, including, but not limited to Kalman filtering, transfer function use, integration, differentiation, and amplification. Filtering methods are performed as many times as desired. In one embodiment, conditioning 96 includes amplification. Amplification may result from a gain of any nonzero number, including by a unity gain. In addition, conditioning 96 may also be realized by any combination and order of filtering, integration, differentiation, and amplification. Filtering is employed for multiple uses including reduction of noise in state measurements 94, reduction of inaccuracies in state measurements 94, or alteration of state measurements 94. For example, alteration of state measurements 94 is performed in a manner similar to integration or differentiation such that drift in numerical integration or noise in numerical differentiation is eliminated.

Conditioned state measurements 100 are transformed using control system 50 to yield transformed state measurements 104. The step of transforming 102 conditioned state measurements 100 is generally described as changing coordinate systems to yield transformed state measurements 104, which are realized by isometric or non-isometric transformations. The types of transformations for changing coordinate systems include rotations and dilations. Other types of transformations include identity transformations, orthogonal projections, oblique projections, changes to other coordinate systems, and changes of scale. In addition, other coordinate systems include polar coordinate systems, barycentric coordinate systems, and similar types of coordinate systems. Changes of scale include log scale or any other function of scale. Moreover, the transformations may include any transformation where transformed state measurements 104 are any mathematical function of conditioned state measurements 100, or any combination in any order of transformations, projections, changes of coordinate system, changes of scale, or other mathematical function.

A transformed state measurement coordinate system is not restricted to have the same number of dimensions as the conditioned state measurement coordinate system. In fact, there may be more or less transformed state measurements 104 than conditioned state measurements 100. Transformation is generally employed so that a robust relationship between conditioned state measurements 100 and a desired output, reference command 122, is found. In an alternative embodiment, the step of transforming 102 is performed prior to the step of conditioning 96. State measurements 94 are transformed using control system 50 to yield transformed state measurements 104. Transformed state measurements 104 then undergo conditioning 96. Transformed state measurements 104 are conditioned using control system 50 to yield conditioned state measurements 100. In either embodiment, conditioning 96 prior to transforming 102 or transforming 102 prior to conditioning 96, the result is a conditioned and transformed state measurement.

Transformed state measurements 104 are used as arguments in one or more reference functions 120. Transformed state measurements 104 are used to calculate reference commands 122 using reference functions 120. Alternatively, conditioned state measurements 100 are used as arguments in one or more reference functions 120. Conditioned state measurements 100 are used to calculate reference commands 122 using reference functions 120.

Each reference function 120 is a function that relates transformed state measurements 104 or conditioned state measurements 100 as independent variables to reference command 122 as a dependent variable. Reference function 120 is represented with a function that accepts inputs and that outputs a unique value for each combination of inputs. Reference function 120 includes look up tables, mathematical functions, or combinations of tables and mathematical functions, or other suitable method. In one embodiment, reference function 120 is determined by recording data from an able-bodied individual. For example, one or more sensors, similar to sensors 20, are coupled to a test subject to detect physical states, such as kinematic or loading states, of the test subject. After sensing the physical states of the able-bodied test subject, the data is processed and used for reference function 120. Able-bodied data can be processed using a series of operations, such as converting 92, conditioning 96, and transforming 102 to produce reference function 120. Reference function 120 is produced to match data from one or more gait activities. Such activities include walking, running, traversing slopes or stairs, avoiding obstacles, and other similar activities. In one embodiment, transformed state measurements 104 are combined with a recording or a calculation of a desired reference command 122. Reference command 122 is an output of control system 50.

The resulting reference command 122, produced by inputting transformed state measurements 104 into reference function 120, is used as an input for actuator 40. Control system 50 is a continuous function relating the position of actuator 40 to a measured signal. The continuous nature of control system 50 eliminates decision making by the system, if-then logic, and changes in state. An invariant signal, such as shank angle, is used to control the gait device. By measuring kinematic or leading states, control system 50 adapts to changes in gait. Control system 50 continuously calculates an output, rather than waiting on a gait event to trigger an output. Because the measured signal and output are related by a continuous function, the output is smooth. The measured signal is phase locked to the user's gait, and thus, the output of control system 50 is phase locked to the user's gait rather than being time based. Because control system 50 is not time-based, control system 50 better adapts to changes in gait.

Figure 6:
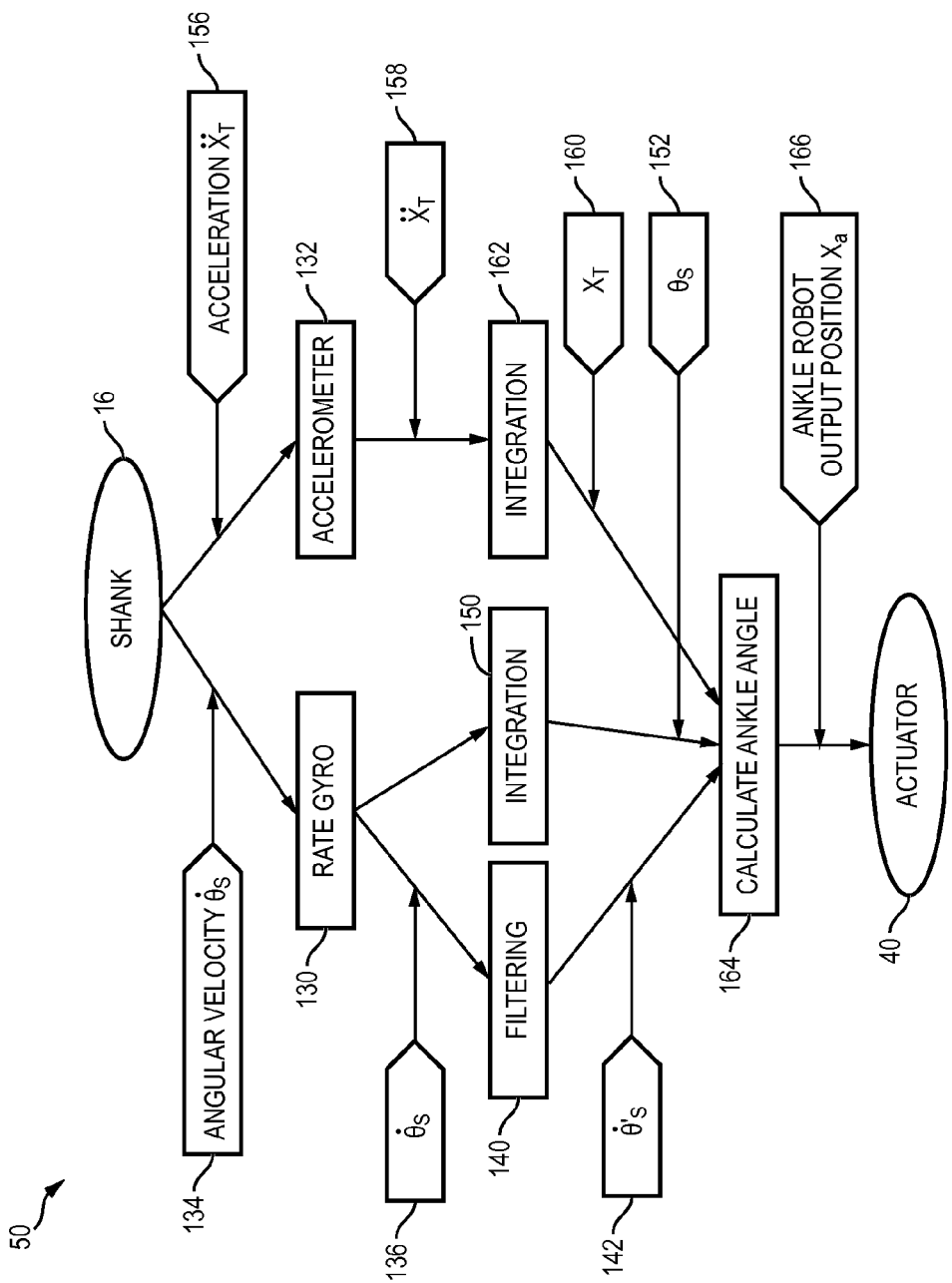
FIG. 6 illustrates a block diagram of a method for controlling gait devices using a control system.

FIG. 6 shows a block diagram showing a method for controlling gait devices using control system 50 to control actuator 40 of ankle prosthesis 14. A plurality of sensors is disposed on shank portion 16. A rate gyro 130 and an accelerometer 132 are coupled to shank portion 16. Rate gyro 130 measures the angular velocity $\dot{\theta}_s$ kinematic state 134 of shank portion 16 in the sagittal direction 30. Rate gyro 130 produces an angular velocity $\dot{\theta}_s$ state measurement 136. The angular velocity $\dot{\theta}_s$ state measurement 136 from rate gyro 130 is conditioned by control system 50 during a filtering 140 step. Filtering 140 comprises a conditioning step and includes one or more filtering methods including Kalman filtering, transfer function use, integration, differentiation, amplification, or combination of filtering methods. Filtering 140 angular velocity $\dot{\theta}_s$ state measurement 136 results in an angular velocity conditioned state measurement 142. Angular velocity $\dot{\theta}_s$ conditioned state measurement 142 is used as an argument in reference function 164. Angular velocity $\dot{\theta}_s$ state measurement 136 from rate gyro 130 is also conditioned by an integration 150 step performed by control system 50 to obtain an angle $\theta_s$ conditioned state measurement 152. Integration 150 is a conditioning step that results in an angular position or angle $\theta_s$ conditioned state measurement 152, which is used as an argument in reference function 164.

Accelerometer 132 measures acceleration $\ddot{X}_T$ kinematic state 156 of shank portion 16 in the transverse direction 34. Accelerometer 132 produces an acceleration $\ddot{X}_T$ state measurement 158. Acceleration $\ddot{X}_T$ state measurement 158 is conditioned to produce a position $X_T$ conditioned state measurement 160. The conditioning step includes one or more filtering methods including Kalman filtering, transfer function use, integration, differentiation, amplification, or combination of filtering methods. In one embodiment, acceleration $\ddot{X}_T$ state measurement 158 from accelerometer 132 is conditioned by double integration 162 by control system 50. Double integration 162 of acceleration $\ddot{X}_T$ is a conditioning step that yields in a position $X_T$ conditioned state measurement 160, such as linear position $X_T$, which is used as an argument in reference function 164 to calculate ankle angle. Other conditioning steps may be used, for example, single integration of acceleration $\ddot{X}_T$ to produce liner velocity $\dot{X}_T$.

An optional transformation step is performed on angular velocity $\dot{\theta}_s'$ conditioned state measurement 142, angle $\theta_s$ conditioned state measurement 152, and position $X_T$ conditioned state measurement 160 after the conditioning steps. Transformation includes changing coordinate system, such as by isometric or non-isometric transformations. The types of transformations for changing coordinate systems include rotations and dilations. Other types of transformations include identity transformations, orthogonal projections, oblique projections, changes to other coordinate systems, and changes of scale. In addition, other coordinate systems include polar coordinate systems, barycentric coordinate systems, and similar types of coordinate systems. Changes of scale include log scale or any other function of scale. In one embodiment, velocity or angular velocity $\dot{\theta}$ is plotted on an x-axis and position $\dot{X}$ or angle $\theta$ is plotted on a y-axis in rectangular coordinates to form a phase plot. The phase plot in rectangular coordinates is used to transform the signal to polar coordinates. Therefore, condition state measurements 142, 152, and 160 are each transformed by identity transformation, and results in no change to condition state measurements 142, 152, and 160 other than the coordinate system. Transformation into polar coordinates results in a polar angle $\phi$ and polar radius R of the measurements, which are used to calculate a desired position or angle for ankle prosthesis 14. Where a transformation step is not used, the calculation of the desired position or angle for ankle prosthesis 14 is simplified. Conditioned state measurements 142, 152, and 160 are input directly into reference function 164 to obtain reference command 166.

The angular velocity $\dot{\theta}_s$' conditioned state measurement 142, angle $\theta_s$ conditioned state measurement 152, and position $X_T$ conditioned state measurement 160 are used to calculate a desired position or angle for ankle prosthesis 14. The position of actuator 40 needed to produce the desired ankle position or ankle angle for ankle prosthesis 14 is calculated using control system 50. The condition state measurements 142, 152, and 160 are used as arguments in reference function 164. Control system 50 generates reference command 166, which relates to an output position $X_a$ for actuator 40. Reference command 166 is used by actuator 40 to position ankle prosthesis 14 to match able-bodied gait data.

Figure 7:
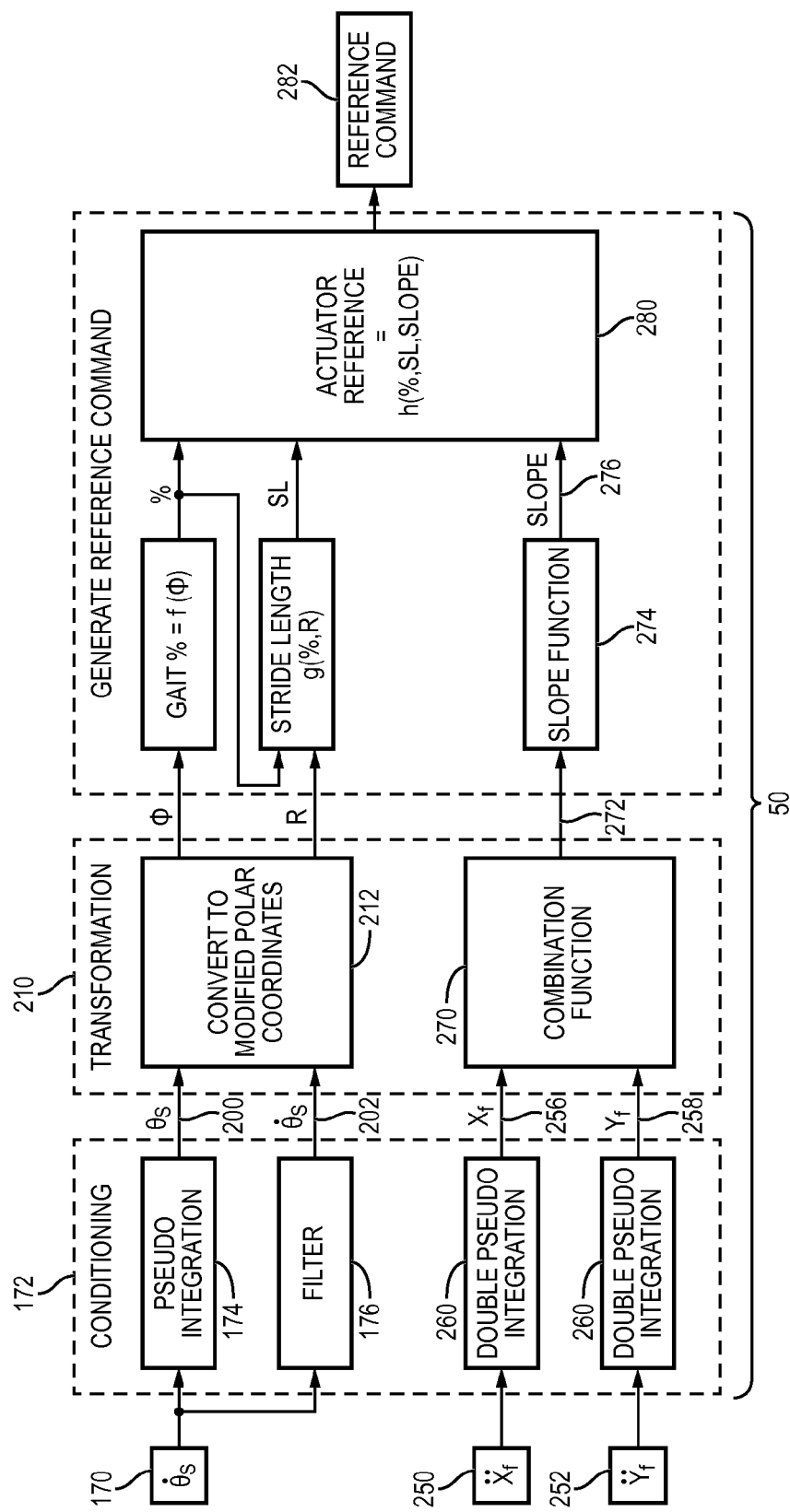
FIG. 7 illustrates a block diagram showing another method for controlling gait devices using a control system.

FIG. 7 shows a block diagram showing another method for controlling gait devices using control system 50. In one embodiment, control system 50 is used to control actuator 40 of ankle prosthesis 14. A plurality of sensors is disposed on user 10 to measure one or more kinematic states of user 10. A rate gyro 130 is disposed on shank portion 16 and an accelerometer 132 is disposed on foot portion 18. Rate gyro 130 measures an angular velocity $\dot{\theta}_s$ kinematic state of shank portion 16 and produces angular velocity $\dot{\theta}_s$ state measurement 170 of shank portion 16. State measurement 170 is conditioned by control system 50. Conditioning 172 of angular velocity $\dot{\theta}_s$ state measurement 170 is realized by pseudo integration 174 and filtering 176.

Figure 8:
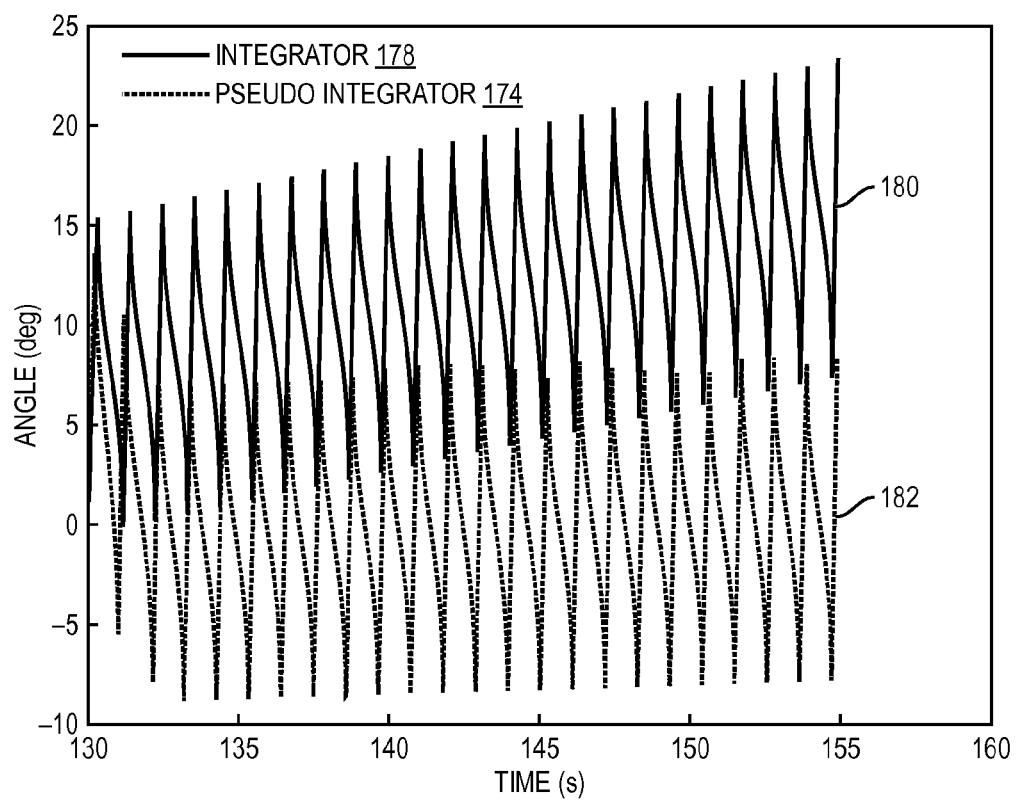
FIG. 8 illustrates a plot comparing two methods of conditioning physical state measurements.

FIG. 8 shows a plot comparing two methods of conditioning physical state measurements received from one or more sensors. Two methods of conditioning 172 a physical state measurement include integration 178 and pseudo integration 174. Pseudo integration 174 uses a transfer function to condition the signal from rate gyro 130. In one embodiment, the transfer function shown in equation (1) is used to integrate angular velocity $\dot{\theta}_s$ state measurement 170 to obtain an angle $\theta_s$ of shank portion 16.

$$T(s)=s/(s+\tau)^2 \tag{1}$$

Where: s=signal
τ=repeated poles

Angle $\theta_s$ of shank portion 16 obtained from pseudo integration 174 is a conditioned state measurement. The transfer function shown in equation (1) used for pseudo integration 174 results in a better conditioned signal than simple integration 178, which is shown in equation (2).

$$T(s)=1/s \tag{2}$$

Integrating angular velocity $\dot{\theta}_s$ state measurement 170 using equation (2) results in signal drift, as shown by line 180. After integration 178, the signal is reliable for short durations, for example, less than 1 second (sec), because of noise and error in measurement. Pseudo integration 174 preserves the shape of the signal as compared to an integrator, but eliminates the drift, as shown by line 182. Since drift is a slow frequency phenomenon, the drift is removed by pseudo integration 174 and the output of pseudo integration 174 is pulled to be centered around zero, making the signal more reliable.

Figure 9:
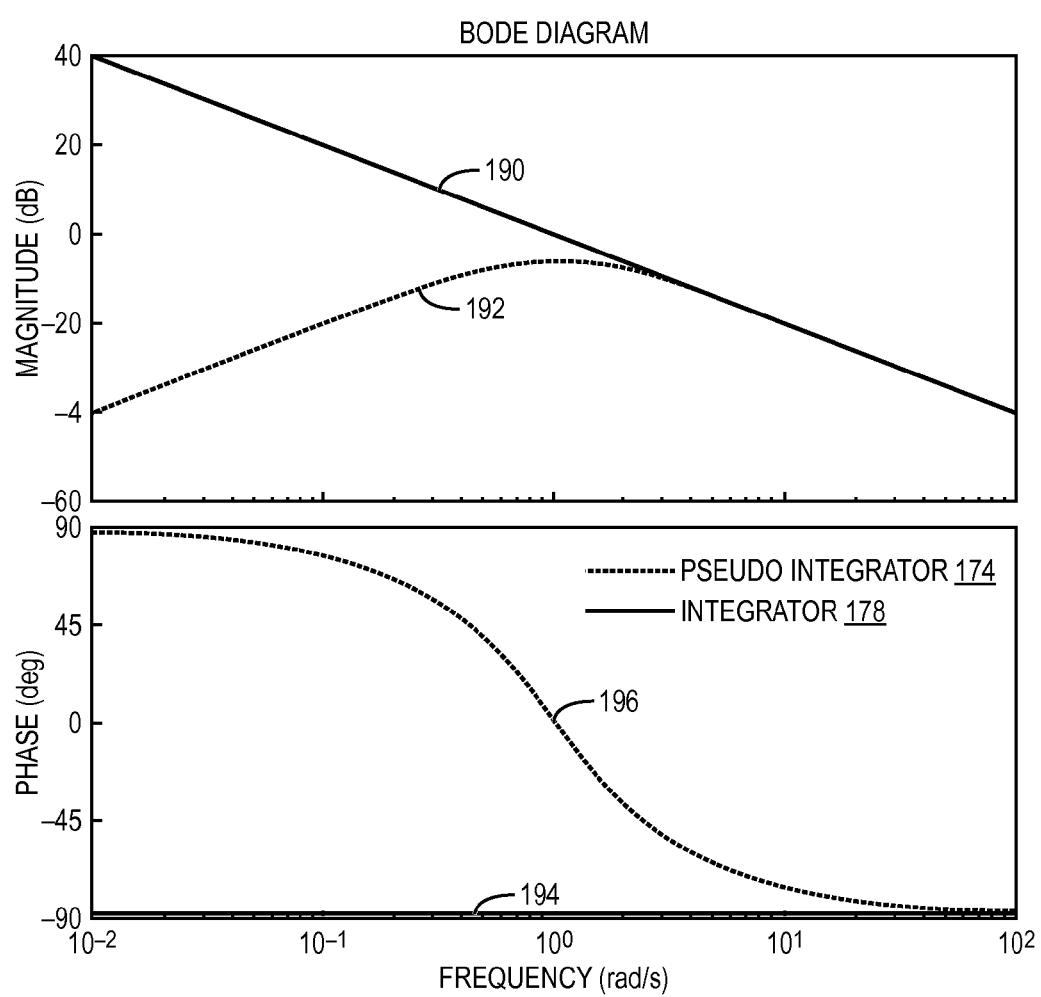
FIG. 9 illustrates a bode plot of a transfer function used for pseudo integration.

FIG. 9 shows bode plots of the transfer function used for pseudo integration 174. In one embodiment, pseudo integration 174 employs the transfer function in equation (1). The choice of the repeated poles τ determines the performance of the transfer function. Frequencies below the repeated poles τ are attenuated. For frequencies above the repeated poles τ, the transfer function behaves similarly to integration 178. Thus, the value of the repeated poles τ defines the cutoff frequency of the transfer function. The cutoff frequency defines how the transfer function behaves at the frequencies above and below the cutoff. In one embodiment, a cutoff for equation (1) is chosen where repeated pole τ is 1 radians/sec. The cutoff is selected such that the frequencies above the cutoff are useful to the signal being measured, and frequencies below the cutoff are not necessary to the signal being measured. For pseudo integration 174 using the transfer function in equation (1) and a cutoff of τ=1, pseudo integration 174 behaves similarly to integration 178 for frequencies above the cutoff, and attenuates the signal for frequencies below the cutoff.

Line 190 represents the magnitude of the signal after integration 178. Integration 178 amplifies the signal at low frequencies. Because drift is a slow frequency, integration 178 amplifies drift, which is undesirable in control system 50. By contrast, pseudo integration 174 attenuates slow frequencies, such as drift. Line 192 shows the magnitude of the signal after pseudo integration 174. Pseudo integration 174 matches integration 178 of the signal at high frequencies, which are the useful frequencies for control system 50.

The phase lag of integration 178 is shown by line 194. Integration 178 lags by 90 degrees at all frequencies. By contrast, pseudo integration 174 has a phase lead of 90 degrees at low frequencies and a phase lag of −90 degrees at high frequencies. The phase of pseudo integration 174 is shown by line 196. Importantly, the phase lag of pseudo integration 174 matches the phase lag of integration 178 at high frequencies, which are the useful frequencies for control system 50. At low frequencies, the signal is attenuated by pseudo integration 174. Therefore, the phase lead of pseudo integration 174 at low frequencies does not affect the performance of control system 50, because the low frequency signals are attenuated.

Returning to FIG. 7, the step of pseudo integration 174 results in an angle $\theta_s$ conditioned state measurement 200. Conditioning 172 further includes the step of filtering 176 angular velocity $\dot{\theta}_s$ state measurement 170. Filtering 176 of angular velocity $\dot{\theta}_s$ state measurement 170 results in an angular velocity $\dot{\theta}_s$' conditioned state measurement 202. In one embodiment, filtering 176 includes a first order filter used to eliminate noise in the signal from rate gyro 130. In another embodiment, conditioning 172 is realized by any filtering method, including, but not limited to Kalman filtering, transfer function use, integration, differentiation, amplification, and any combination of the filtering methods. Filtering 176 is performed as many times as desired. Filtering 176 is employed for multiple uses including reduction of noise, reduction of inaccuracies, or alteration of angular velocity $\dot{\theta}_s$ state measurement 170.

In one embodiment, filtering 176 includes a pseudo integration step, similar to pseudo integration 174, followed by a pseudo differentiation step. Pseudo integration centers the signal, angular velocity $\dot{\theta}_s$ conditioned state measurement, around zero. Centering the signal at zero ensures small differences in the user's gait do not negatively affect control system 50. Because a user performs many different gait activities, such a walking, running, or going up or down stairs or slopes, a sensor disposed on the user will have different starting positions. Conditioning 172 of angular velocity $\dot{\theta}_s$ state measurement 170 by pseudo integration 174 and filtering 176 ensures control system 50 works for each gait activity. In addition to centering the signal around zero, pseudo integration also integrates the signal. Pseudo integration of angular velocity $\dot{\theta}_s$ kinematic state measurement 170 results in an angular position or angle $\theta_s$ conditioned state measurement. After pseudo integration, the signal is pseudo differentiated. Pseudo differentiation of the angle $\theta_s$ conditioned state measurement results in an angular velocity $\dot{\theta}_s'$ conditioned state measurement 202. An advantage of pseudo differentiation over standard differentiation is that noise is attenuated. For pseudo differentiation using a transfer function, high frequency signals are attenuated and are unimportant for control system 50. For low frequencies, transfer functions behave similarly to standard differentiation. By combining the pseudo integration and pseudo differentiation, the signal is centered, noise attenuated, and the useful information in the signal retained. A pseudo differentiator includes any transfer function that behaves as a differentiator at low frequencies and attenuates the input at high frequencies.

In another embodiment, filtering 176 includes a bandpass filter. The bandpass filter is used to attenuate noise at frequencies above the useful frequencies of the signal and to attenuate noise at frequencies below the useful frequencies of the signal. Therefore, the bandpass filter acts to center the signal and eliminate noise.

After conditioning 172, an optional transformation 210 step is performed on angle $\theta_s$ conditioned state measurement 200 and angular velocity $\dot{\theta}_s'$ conditioned state measurement 202. Transformation 210 includes changing coordinate system, such as by isometric or non-isometric transformations. The types of transformations for changing coordinate systems include rotations and dilations. Other types of transformations include identity transformations, orthogonal projections, oblique projections, changes to other coordinate systems, and changes of scale. In addition, other coordinate systems include polar coordinate systems, barycentric coordinate systems, and similar types of coordinate systems. Changes of scale include log scale or any other function of scale. In one embodiment, transformation 210 includes a step of converting 212 the coordinate system of the signals to modified polar coordinates, polar angle $\phi$ and polar radius R.

Figure 10:
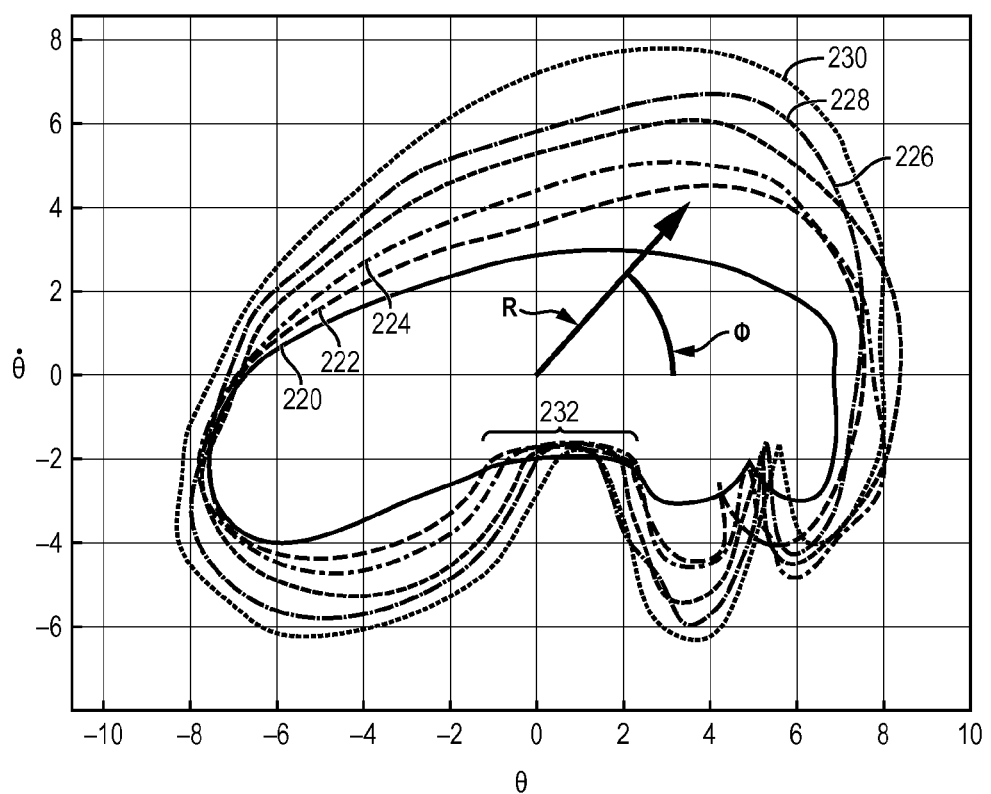
FIG. 10 illustrates a phase plot of angle and angular velocity at different speeds of gait.

FIG. 10 shows a phase plot of angle and angular velocity at different speeds of gait. The physical state measurements are converted to modified polar coordinates. Angular velocity $\dot{\theta}_s'$ conditioned state measurement 202 is depicted as angular velocity $\dot{\theta}$ in the phase plot and is plotted on the x-axis. Angle $\theta_s$ conditioned state measurement 200 is depicted as angle $\theta$ in the phase plot and is plotted on the y-axis in rectangular coordinates. The plot shows changes in angle $\theta$ and angular velocity $\dot{\theta}$ for shank portion 16 as user 10 walks through a gait cycle. The plot shows full gait cycles for user 10 walking at various speeds, where each line 220, 222, 224, 226, 228, and 230 represents a different speed of gait. For example, line 220 represents a gait cycle for a slower walking speed than line 222. Line 230 shows fast gait speed. Each line 220, 222, 224, 226, 228, and 230 represents a full gait cycle. Region 232 shows how the signals overlap during stance phase of gait.

The phase plot shows the polar coordinates, polar angle $\phi$ and polar radius R, for gait cycles of user 10. Polar angle $\phi$ and polar radius R are calculated from angular velocity $\dot{\theta}$ and angle $\theta$ of shank portion 16. Polar angle $\phi$ corresponds to progression through the gait cycle, also referred to as the percentage of gait cycle or gait percent (gait %). Polar radius R corresponds to stride length SL during the user's gait or to the pace of the user's gait. Polar angle $\phi$ and polar radius R are used to calculate a desired output position for an actuator of a gait device. Based on the desired position for ankle prosthesis 14, control system 40 produces reference command 122 for actuator 40 to control ankle prosthesis 14.

Angular velocity $\dot{\theta}_s'$ conditioned state measurement 202 and angle $\theta_s$ conditioned state measurement 200, depicted as angular velocity $\dot{\theta}$ and angle $\theta$ respectively, are adjusted to produce the phase plot. In one embodiment, angular velocity $\dot{\theta}$ of shank portion 16 is adjusted by dividing by a scaling factor and subtracting a shifting constant. Angular velocity $\dot{\theta}$ is scaled so that the magnitude of the angular velocity $\dot{\theta}$ signal is approximately the same as the magnitude of angle $\theta$. Angular velocity $\dot{\theta}$ is shifted down by the shifting constant to prevent control system 50 from moving through the entire gait cycle while user 10 is standing still. During stance phase of gait, angular velocity $\dot{\theta}$ measured at shank portion 16 can slow to almost zero while the user's foot is planted on the ground. Angular velocity $\dot{\theta}$ is also close to zero while user 10 stands still. Control system 50 differentiates between an angular velocity $\dot{\theta}$ of zero during stance phase and the user's angular velocity $\dot{\theta}$ of zero while standing still. Because user 10 does not stand still without any movement, and sensors output noise, angle $\theta$ and angular velocity $\dot{\theta}$ move quickly around the origin of the phase plot. Without a shifting constant, control system 50 follows polar angle $\phi$ through a gait cycle from zero to 360 degrees and moves actuator 40 quickly through an entire gait cycle. By shifting the angular velocity $\dot{\theta}$ down, polar angle $\phi$ is stabilized while user stands still and during stance phase. Control system 50 can thus reliably produce an output that directs actuator 40 to remain still while user 10 stands still, but also produce the correct output during stance phase of a gait cycle.

Returning again to FIG. 7, polar angle $\phi$ and polar radius R are used as arguments for reference function. Gait percent or gait progression indicates what stage user 10 is in the gait cycle. Gait percent related to the polar angle $\phi$ of the phase plot by a function of polar angle $\phi$ as shown generally in equation (3). Stride length SL and gait percent are related to polar radius R as shown generally in equation (4).

$$\text{Gait \%} = f(\phi) \tag{3}$$

$$SL = g(\text{gait \%}, R) \tag{4}$$

Figure 11:
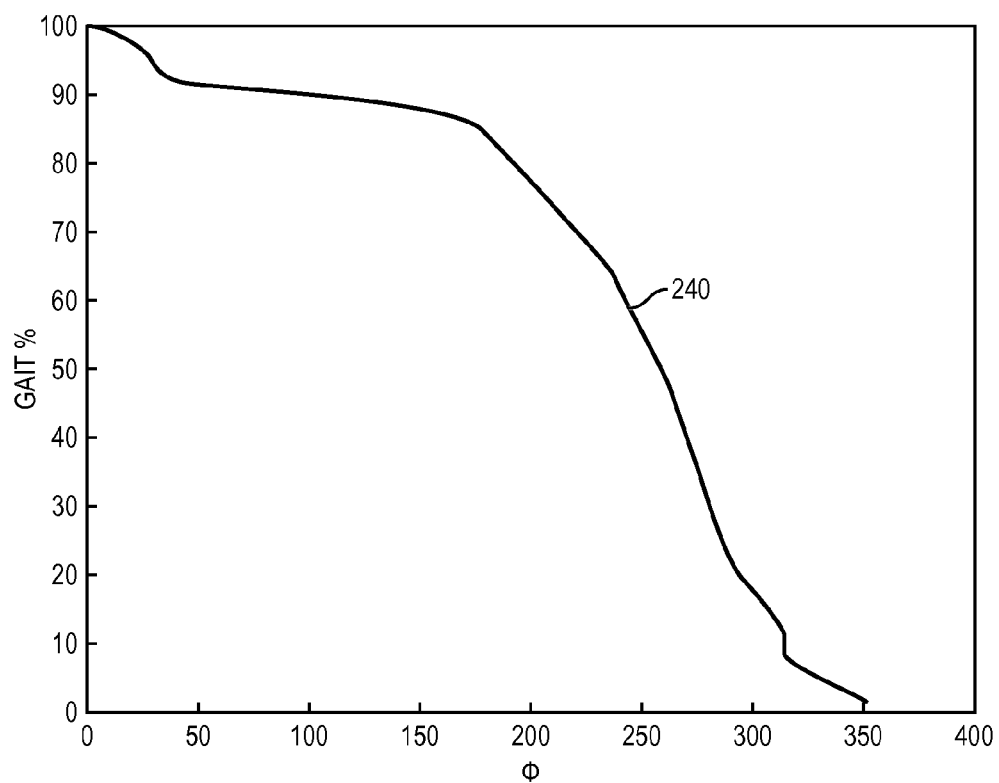
FIG. 11 illustrates a plot of gait percent as a function of polar angle.

FIG. 11 illustrates a phase plot of gait percent as a function of polar angle $\phi$. Line 240 shows the correlation between gait percent and polar angle $\phi$. Because the phase plots for different gait speeds are of similar shape, the relationship between polar angle and gait percent is approximately the same for all speeds. Equation (3) is represented as a mathematical relation, a lookup table of values, or any suitable similar method.

Figure 12:
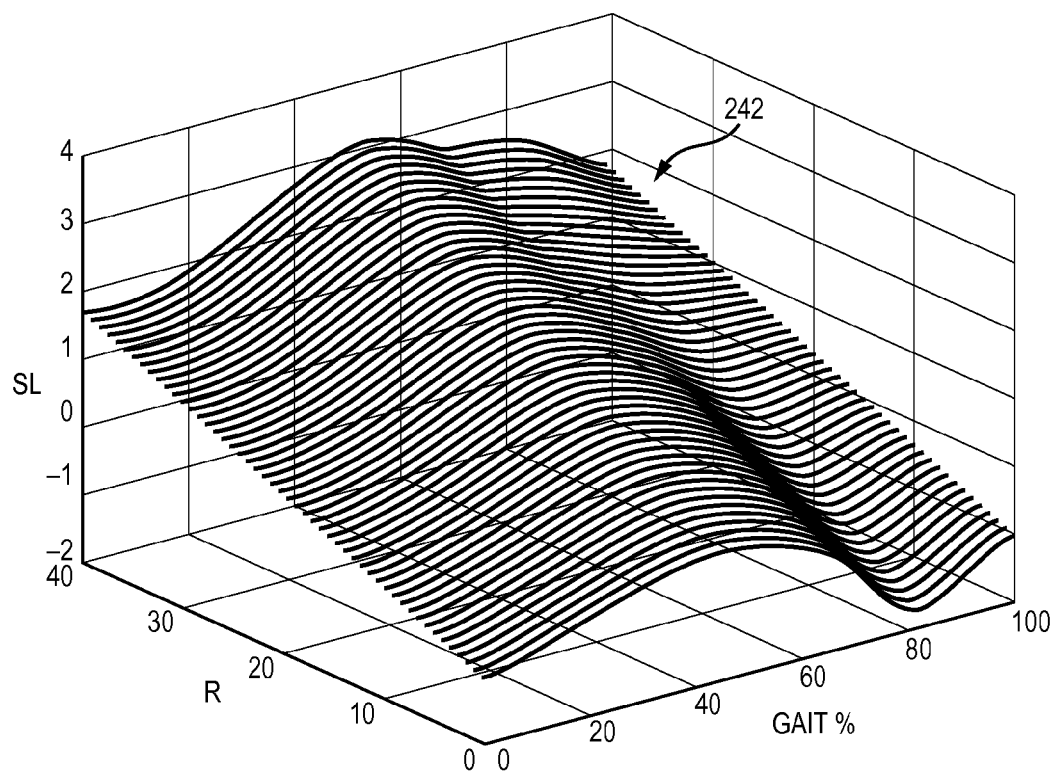
FIG. 12 illustrates a plot of stride length as a function of gait percent and polar radius.

FIG. 12 shows a phase plot of stride length SL related to polar radius R. Gait percent is plotted on an x-axis, polar radius R on a y-axis, and stride length SL on a z-axis. Plane 242 shows the correlation between stride length SL, gait percent, and polar radius R. Stride length SL is determined as a function of both gait percent and polar radius R. Equation (4) is represented as a mathematical relation, a lookup table of values, or any suitable similar method. In one embodiment, plane 242 is fit with a function or lookup table to determine a position for actuator 40.

Returning again to FIG. 7, the method for controlling gait devices using control system 50 to control actuator 40 of ankle prosthesis 14 further includes accelerometer 132 disposed on foot portion 18. Accelerometer 132 improves the performance of control system 50 by making control system 50 more sensitive to user 10 going up and down slopes and stairs. Accelerometer 132 measures a linear acceleration kinematic state of foot portion 18 in one or more directions, for example, in the sagittal direction 30, coronal direction 32, or transverse direction 34. In one embodiment, accelerometer 132 produces acceleration $\ddot{X}_f$ state measurement 250 in a first direction X and acceleration $\ddot{Y}_f$ state measurement 252 in a second direction Y.

Acceleration $\ddot{X}_f$ state measurement 250 and acceleration $\ddot{Y}_f$ state measurement 252 are conditioned to produce a position $X_f$ conditioned state measurement 256 and position $Y_f$ conditioned state measurement 258 respectively. Conditioning 172 includes one or more filtering methods including Kalman filtering, transfer function use, integration, differentiation, amplification, or combination of filtering methods. In one embodiment, acceleration $\ddot{X}_f$ state measurement 250 from accelerometer 132 is conditioned by double pseudo integration 260 by control system 50. Acceleration $\ddot{Y}_f$ state measurement 252 from accelerometer 132 is also conditioned by double pseudo integration 260 by control system 50. Therefore, conditioning 172 of state measurement 250 and 252 is realized by double pseudo integration 260.

Double pseudo integration 260 employs a transfer function to condition the signals from accelerometer 132. In one embodiment, the transfer function shown in equation (5) is used to double integrate acceleration $\ddot{X}_f$ state measurement 250 and acceleration $\ddot{Y}_f$ state measurement 252 to obtain positions $X_f$ and $Y_f$ of foot portion 18.

$$T(s)=s^{n-2}/(s+\tau)^n \quad (5)$$

Where:
s=signal
τ=repeated poles
n=number of poles

Positions $X_f$ and $Y_f$ of foot portion 18 obtained by double pseudo integration 260 comprise conditioned state measurements 256 and 258. The transfer function shown in equation (5) used for double pseudo integration 260 results in a better conditioned signal than double integration, which is shown in equation (6).

$$T(s)=1/s^2 \quad (6)$$

The choice of the repeated pole T determines the performance of the transfer function in equation (5) used for double pseudo integration 260. The value of the repeated poles τ defines the cutoff frequency for the transfer function. The cutoff frequency defines how the transfer function behaves at frequencies above and below the cutoff. Frequencies below the repeated poles τ are attenuated. For frequencies above the repeated poles τ, the transfer function behaves similarly to double integration in equation (6). In one embodiment, a cutoff for equation (5) is chosen where repeated pole τ is 1 radians/sec. In one embodiment, the cutoff is selected where the frequencies above the cutoff are useful to the signal being measured, and frequencies below the cutoff are not necessary to the signal being measured. For double pseudo integration 260 using the transfer function in equation (5) and a cutoff of τ=1, pseudo integration 260 behaves similarly to double integration for frequencies above the cutoff, and attenuates the signal for frequencies below the cutoff.

The transfer function used for double pseudo integration 260 includes any transfer function that behaves as an integrator at high frequencies and attenuates the input at low frequencies. The poles may be repeated poles or not and the transfer function can take many forms. In another embodiment, the transfer function is an elliptical transfer function having a sharp cutoff such that the transition is sharp from integration to attenuation.

After conditioning 172, a transformation 210 step is performed on position $X_f$ conditioned state measurement 256 and position $Y_f$ conditioned state measurement 258. Transformation 210 includes changing coordinate system, such as by isometric or non-isometric transformations. The types of transformations for changing coordinate systems include rotations and dilations. Other types of transformations include identity transformations, orthogonal projections, oblique projections, changes to other coordinate systems, and changes of scale. In addition, other coordinate systems include polar coordinate systems, barycentric coordinate systems, and similar types of coordinate systems. Changes of scale include log scale or any other function of scale. In one embodiment, transformation 210 includes a combination function 270, which uses the curvature and instantaneous radius of the signal to determine slope, where the shape of the curve is independent from the magnitude. The output of the transformation step 210 is a transformed state measurement 272. Transformed state measurement 272 is then input into a slope function 274 to produce slope 276, which is ultimately used as an argument in reference function 280.

Gait percent and stride length SL from equations (3) and (4) are also used as arguments in reference function 280. Gait percent or gait progression indicates what stage user 10 is in the gait cycle and is related to the polar angle φ of the phase plot by a function of polar angle φ as shown generally in equation (3). Stride length SL and gait percent are related to polar radius R as shown generally in equation (4). Stride length SL is determined as a function of both gait percent and polar radius R.

Reference function 280 is a function that relates slope 276, stride length SL, and gait percent as independent variables to reference command 282 as a dependent variable, shown generally in equation (7). Actuator position $X_a$ is determined by inputting slope 276, stride length SL, and gait percent into reference function 280.

$$X_a=h(\text{gait \%},SL,\text{slope}) \quad (7)$$

Where: $X_a$=actuator position

Reference function 280 is represented with a function that accepts inputs and that outputs a unique value for each combination of inputs. An actuator position $X_a$ is known for each gait percent and stride length SL as shown generally in equation (8). In one embodiment, reference function 280 is represented as a mathematical relation, a lookup table of values, or any suitable similar method.

$$X_a=h(\text{gait \%},SL) \quad (8)$$

Reference function 280 is based on able bodied data and is produced to match data from one or more gait activities. Such activities include walking, running, traversing slopes or stairs, avoiding obstacles, and other similar activities. An actuator position $X_a$ is predetermined for each stride length SL and gait percent through collection of able-bodied gait data and calculation of geometry for ankle prosthesis 14 to determine how actuator 40 should move. Based on stride length SL and gait percent, control system 50 matches the desired actuator position $X_a$ to the of able-bodied gait data and generates reference command 282 to control the position of actuator 40 to match the able-bodied gait data.

Figure 13:
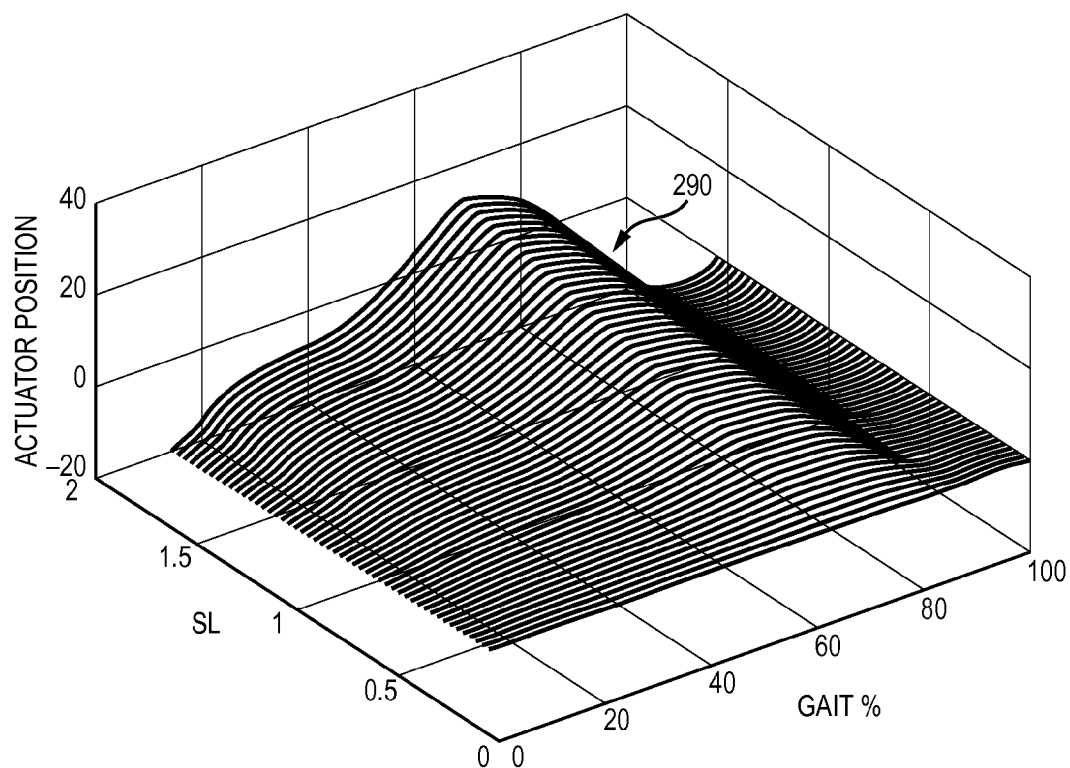
FIG. 13 illustrates a plot of actuator position as a function of gait percent and stride length.

FIG. 13 shows a plot of a reference function relating stride length SL as a function of gait percent and polar radius. Reference function 280 is based on able bodied data and is produced to match data from one or more gait activities. Such activities include walking, running, traversing slopes or stairs, avoiding obstacles, and other similar activities. An actuator position $X_a$ is predetermined for each stride length SL and gait percent through collection of able-bodied gait data and calculation of geometry for ankle prosthesis 14 to determine how actuator 40 should move. Gait percent is plotted on an x-axis, stride length SL on a y-axis, and actuator position $X_a$ on a z-axis. Based on stride length SL and gait percent, control system 50 looks up the desired actuator position $X_a$ and generates reference command 282 to control the position of actuator 40. In one embodiment, reference function 280 is based on gait data for walking and is shown by plane 290. Plane 290 shows the correlation between actuator position $X_a$ and stride length SL and gait percent as calculated from angular velocity $\dot{\theta}_s'$ state measurement 170 of shank portion 16 of lower leg prosthesis 12.

Figure 14:
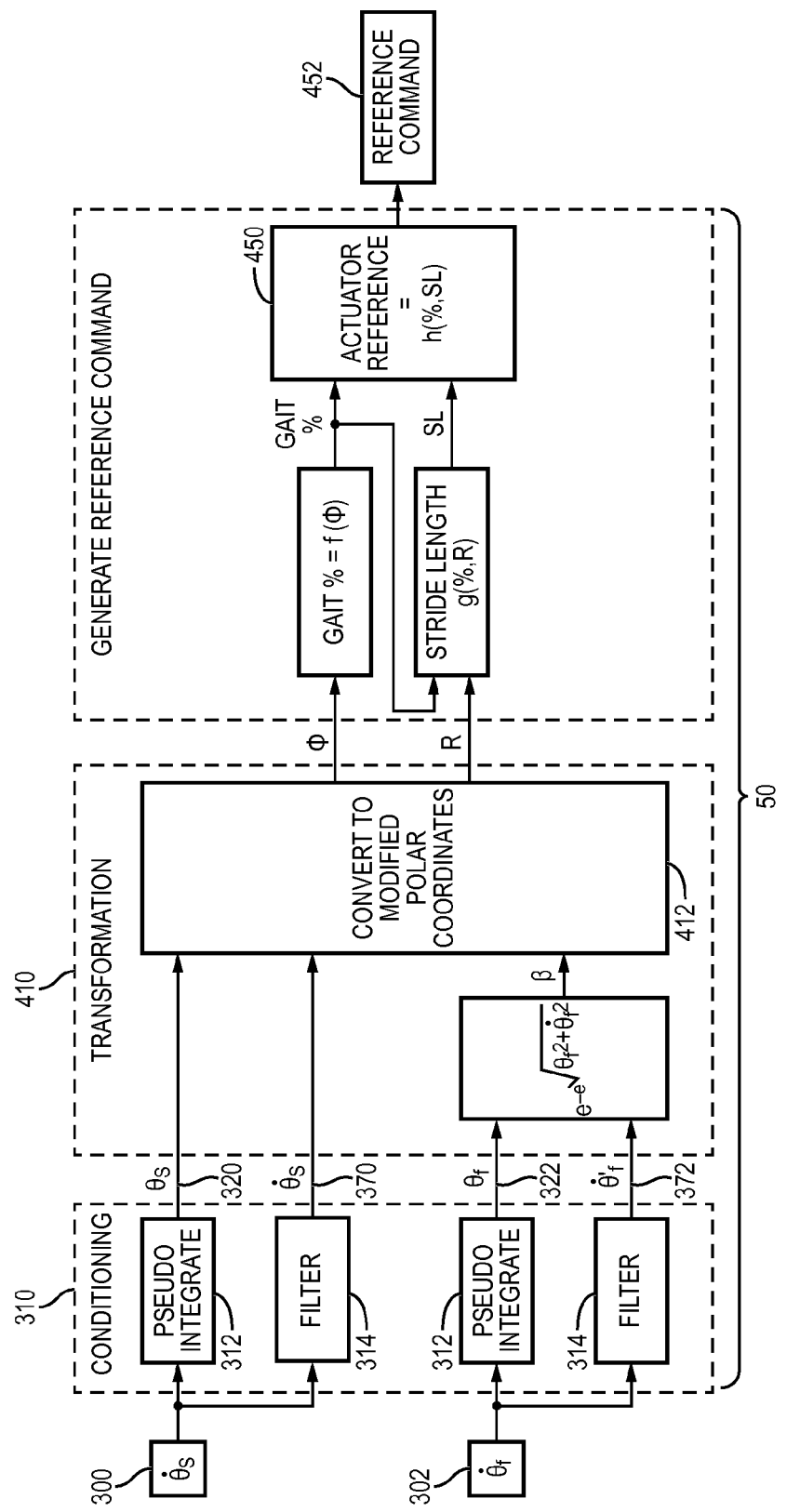
FIG. 14 illustrates a block diagram of an alternative control system and method for controlling gait devices.

FIG. 14 shows a block diagram of an alternative control system and method for controlling gait devices. A plurality of sensors is disposed on user 10 to measure one or more kinematic states of user 10. A first sensor, such as rate gyro 130, is disposed on shank portion 16. A second sensor, such as rate gyro 130, is disposed on foot portion 18. Rate gyro 130 disposed on shank portion 16 measures an angular velocity $\dot{\theta}_s$ kinematic state of shank portion 16 to produce angular velocity $\dot{\theta}_s$ state measurement 300 of shank portion 16. Rate gyro 130 disposed on foot portion 18 measures an angular velocity $\dot{\theta}_f$ kinematic state of foot portion 18 to produce angular velocity $\dot{\theta}_f$ state measurement 302. State measurements 300 and 302 are conditioned by control system 50. Conditioning 310 of angular velocity $\dot{\theta}_s$ state measurement 300 is realized by pseudo integration 312 and filtering 314. Similarly, conditioning 310 of angular velocity $\dot{\theta}_f$ state measurement 302 is realized by pseudo integration 312 and filtering 314.

Pseudo integration 312 uses a transfer function to condition the signal from rate gyro 130. In one embodiment, the transfer function shown in equation (9) is used to condition angular velocity $\dot{\theta}_s$ state measurement 300 to obtain an angle $\theta_s$ conditioned state measurement 320 of shank portion 16. The transfer function shown in equation (9) is also used to condition angular velocity $\dot{\theta}_f$ state measurement 302 to obtain a an angle $\theta_f$ conditioned state measurement 322 of foot portion 18.

$$T(s)=s^{n-1}/(s+\tau)^n \quad (9)$$

Where:
s=signal
τ=repeated poles
n=number of poles

Figure 15:
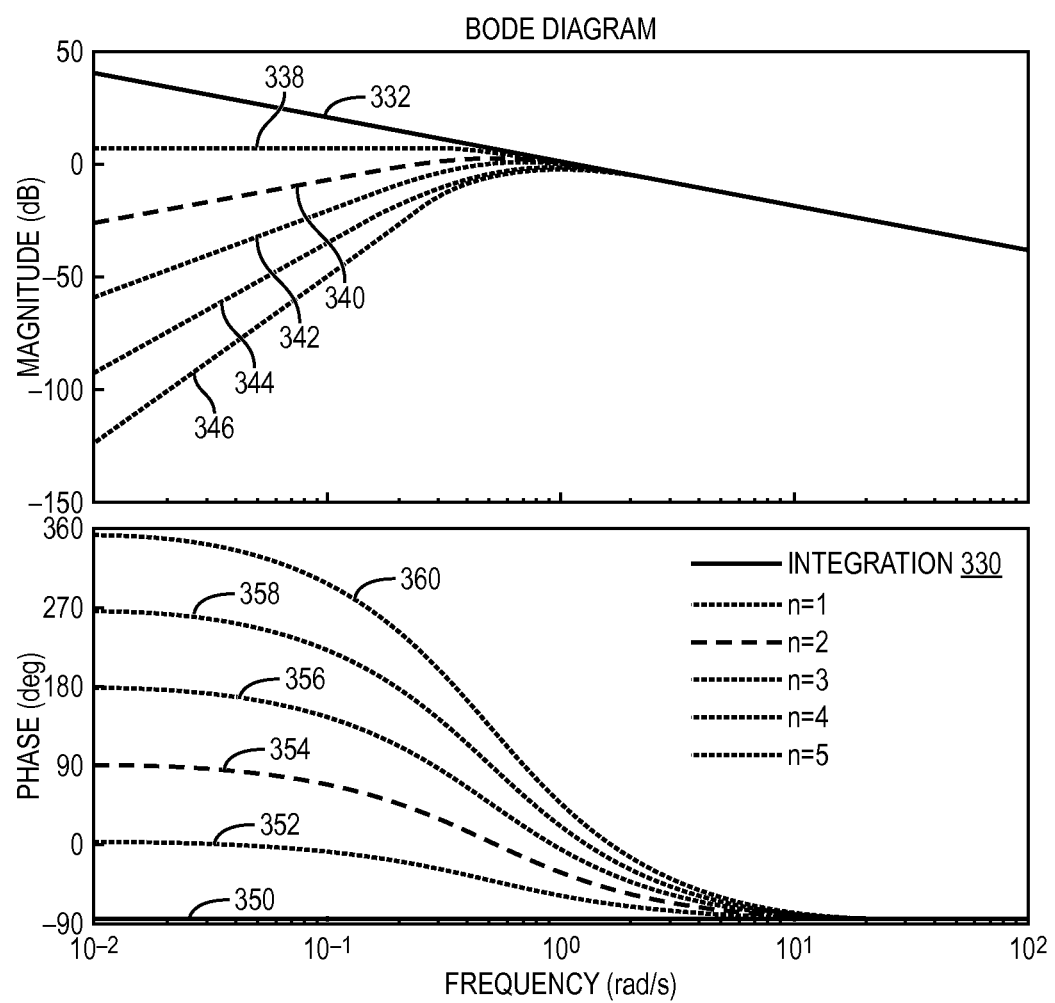
FIG. 15 illustrates a bode plot of transfer functions used for pseudo integration.

FIG. 15 shows bode plots of the transfer function used for pseudo integration 312. The transfer function conditions state measurements 300 and 302 to attenuate the signal at frequencies below repeated poles τ and integrate the signal at frequencies above repeated poles τ. The choice of the repeated pole τ determines the performance of the transfer function in equation (9) used for pseudo integration 312.

Frequencies below the repeated poles τ are attenuated. For frequencies above the repeated poles τ, the transfer function behaves similarly to integration 330, shown in equation (2). The value of the repeated poles τ defines the cutoff frequency for the transfer function. The cutoff frequency defines how the transfer function behaves at the frequencies above and below the cutoff. In one embodiment, the cutoff is selected such that the frequencies above the cutoff are useful to the signal being measured, and frequencies below the cutoff are not necessary to the signal being measured. Using the transfer function in equation (9), pseudo integration 312 behaves similarly to integration 330 for frequencies above the cutoff, and attenuates the signal for frequencies below the cutoff.

Integration 330 is shown by line 332. Integration 330 amplifies the signal at low frequencies. Drift is a slow frequency, and integration amplifies drift, which is undesirable in control system 50. By contrast, pseudo integration 312 attenuates signals at low frequencies, such as drift. Line 338 represents the magnitude of the signal after pseudo integration 312, where the number of poles n is 1. Line 340 represents the magnitude of the signal after pseudo integration 312, where the number of poles n is 2. Line 342 represents the magnitude of the signal after pseudo integration 312, where the number of poles n is 3. Line 344 represents the magnitude of the signal after pseudo integration 312, where the number of poles n is 4. Line 346 represents the magnitude of the signal after pseudo integration 312, where the number of poles n is 5. The behavior of pseudo integration 312 matches integration 330 at high frequencies, which are the useful frequencies for control system 50.

The phase lag of integration 330 is shown by line 350. Integration 330 lags by 90 degrees at all frequencies. By contrast, pseudo integration 312 has phase lead or phase lag depending on the frequency. The phase of pseudo integration 312 where the number of poles n is 1 is shown by line 352. The phase of pseudo integration 312 where the number of poles n is 2 is shown by line 354. The phase of pseudo integration 312 where the number of poles n is 3 is shown by line 356. The phase of pseudo integration 312 where the number of poles n is 4 is shown by line 358. The phase of pseudo integration 312 where the number of poles n is 5 is shown by line 360. The phase lag of pseudo integration 312 matches the phase lag of integration 330 at high frequencies, which are the useful frequencies for control system 50. At low frequencies, the signal is attenuated by pseudo integration 312. Therefore, the phase of pseudo integration 312 at low frequencies does not affect the performance of control system 50, because the low frequency signals are attenuated.

Returning to FIG. 14, the step of pseudo integration 312 results in angle $\theta_s$ conditioned state measurement 320 from a shank sensor and angle $\theta_f$ conditioned state measurement 322 from a foot sensor. Conditioning 310 further includes the step of filtering 314 angular velocity $\dot{\theta}_s$ state measurement 300 and angular velocity $\dot{\theta}_f$ state measurement 302. Filtering 314 of angular velocity $\dot{\theta}_s$ state measurement 300 results in an angular velocity $\dot{\theta}_s'$ conditioned state measurement 370. Filtering 314 of angular velocity $\dot{\theta}_s$ state measurement 302 results in an angular velocity $\dot{\theta}_s'$ conditioned state measurement 372.

In one embodiment, filtering 314 includes a first order filter used to eliminate noise in the signal from rate gyros 130. In another embodiment, conditioning 310 is realized by any filtering method, including, but not limited to Kalman filtering, transfer function use, integration, differentiation, amplification, and any combination of the filtering methods. Filtering 314 is performed as many times as desired. Filtering 314 is employed for multiple uses including reduction of noise, reduction of inaccuracies, or alteration of state measurements 300 and 302.

In one embodiment, filtering 314 includes a pseudo integration step, similar to pseudo integration 312, followed by a pseudo differentiation step. Pseudo integration centers the signal, angular velocity $\dot{\theta}_s$ conditioned state measurement, around zero. Centering the signal at zero ensures small differences in the user's gait do not negatively affect control system 50. Because a user performs many different gait activities, such as walking, running, or going up or down stairs or slopes, a sensor disposed on the user will have different starting positions. Conditioning 310 of angular velocity $\dot{\theta}_s$ state measurement 300 by pseudo integration 312 and filtering 314 ensures control system 50 works for each gait activity. In addition to centering the signal around zero, pseudo integration also integrates the signal. Pseudo integration of angular velocity $\dot{\theta}_s$ kinematic state measurement 300 results in an angular position of shank portion 16, such as angle $\theta_s$. Pseudo integration of angular velocity $\dot{\theta}_f$ kinematic state measurement 302 results in an angular position of portion 18, such as angle $\theta_f$. After pseudo integration, the signals, angle $\theta_s$ and angle $\theta_f$, are pseudo differentiated. Pseudo differentiation of angle $\theta_s$ results in angular velocity $\dot{\theta}_s'$ conditioned state measurement 370. Pseudo differentiation of angle $\theta_f$ results in angular velocity $\dot{\theta}_f'$ conditioned state measurement 372. An advantage of pseudo differentiation over standard differentiation is that noise is attenuated.

Figure 16:
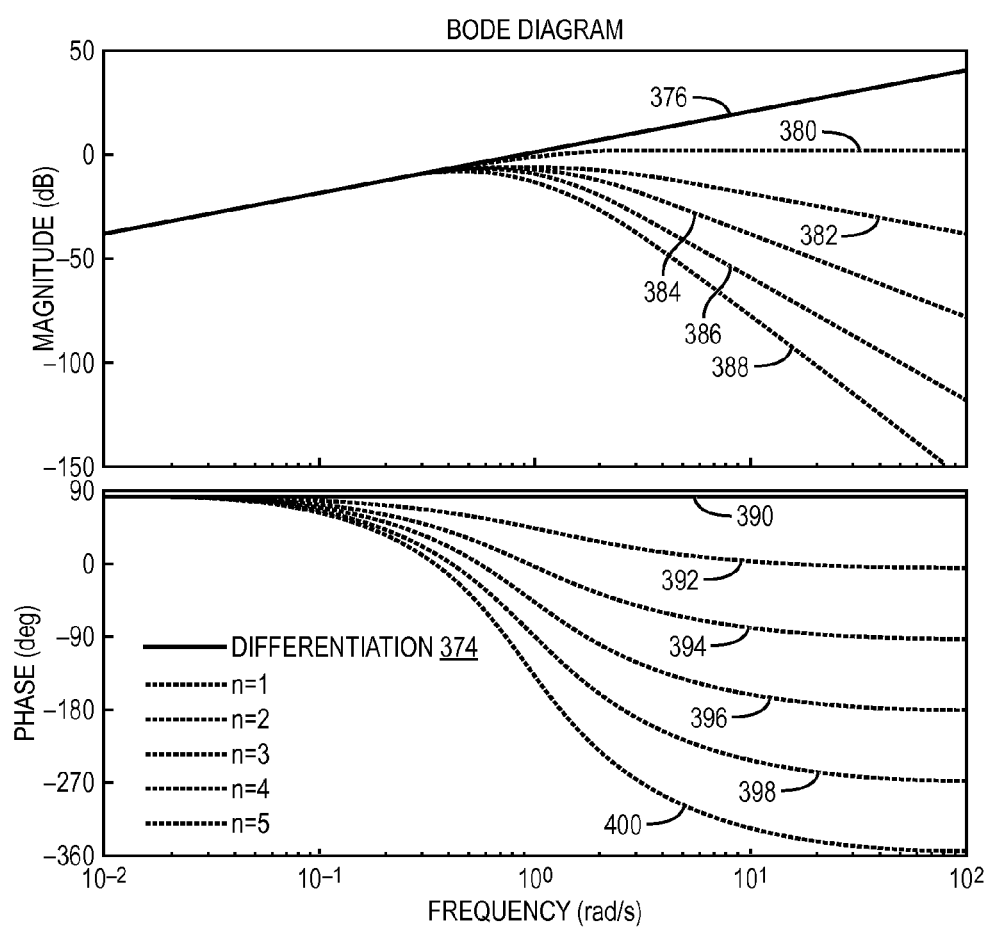
FIG. 16 illustrates a bode plot of transfer functions used for pseudo differentiation.

FIG. 16 shows a bode plot of transfer functions used for pseudo differentiation. Pseudo differentiation uses a transfer function to condition the signals from rate gyros 130. In one embodiment, the transfer function shown in equation (10) is used for pseudo differentiation of angle $\theta_s$ and angle $\theta_f$.

$$T(s)=\tau^n s/(s+\tau)^n \quad (10)$$

Where:
s=signal
τ=repeated poles
n=number of poles

For the pseudo differentiation with the transfer function shown in equation (10), high frequency signals are attenuated. For low frequencies, the transfer function behaves similarly to standard differentiation. A pseudo differentiator includes any transfer function that behaves as a differentiator at low frequencies and attenuates the input at high frequencies.

The transfer function in equation (10) conditions the signal, angle $\theta_s$ and angle $\theta_f$, to attenuate the signal at frequencies above repeated poles τ and differentiate the signal at frequencies below repeated poles τ. The choice of the repeated pole τ determines the performance of the transfer function in equation (10) used for pseudo differentiation. The value of the repeated poles τ defines the cutoff frequency for the transfer function. The cutoff frequency defines how the transfer function behaves at the frequencies above and below the cutoff. In one embodiment, the cutoff is selected such that the frequencies below the cutoff are useful to the signal being measured, and frequencies above the cutoff are not necessary to the signal being measured. For pseudo differentiation, the transfer function in equation (10) behaves similarly to differentiation 374 for frequencies below the cutoff, and attenuates the signal for frequencies above the cutoff. Differentiation 374 is shown by line 376.

Line 380 represents the magnitude of the signal after pseudo differentiation, where the number of poles n is 1. Line 382 represents the magnitude of the signal after pseudo differentiation, where the number of poles n is 2. Line 384 represents the magnitude of the signal after pseudo differentiation, where the number of poles n is 3. Line 386 represents the magnitude of the signal after pseudo differentiation, where the number of poles n is 4. Line 388 represents the magnitude of the signal after pseudo differentiation, where the number of poles n is 5. The behavior of pseudo differentiation matches differentiation 374, line 376, at low frequencies.

The phase lead of differentiation 374 is shown by line 390. Differentiation 374 leads by 90 degrees at all frequencies. By contrast, pseudo differentiation has phase lead or phase lag depending on the frequency. The phase of pseudo differentiation where the number of poles n is 1 is shown by line 392. The phase of pseudo differentiation where the number of poles n is 2 is shown by line 394. The phase of pseudo differentiation where the number of poles n is 3 is shown by line 396. The phase of pseudo differentiation where the number of poles n is 4 is shown by line 398. The phase of pseudo differentiation where the number of poles n is 5 is shown by line 400. The phase lead of pseudo differentiation matches the phase lead of differentiation 374, line 390, at low frequencies, which are the useful frequencies for control system 50. At high frequencies, the signal is attenuated by pseudo differentiation. Therefore, the phase of pseudo differentiation at high frequencies does not affect the performance of control system 50, because the high frequency signals are attenuated. By combining the pseudo integration and pseudo differentiation, the signal is centered, noise attenuated, and the useful information in the signal retained.

Returning to FIG. 14, conditioning 310 results in conditioned state measurements for shank portion 16 and for foot portion 18. Angle $\theta_s$ conditioned state measurement 320 and angular velocity $\dot{\theta}_s'$ conditioned state measurement 370 comprise the conditioned state measurements for shank portion 16. Angle $\theta_f$ conditioned state measurement 322 and angular velocity $\dot{\theta}_f'$ conditioned state measurement 372 comprise the conditioned state measurements for foot portion 18.

After conditioning 310, the conditioned state measurements for shank portion 16 undergo a transformation 410 step. Transformation 410 is performed on angle $\theta_s$ conditioned state measurement 320 and angular velocity $\dot{\theta}_s'$ conditioned state measurement 370. Transformation 410 includes changing the coordinate system, such as by isometric or non-isometric transformations. The types of transformations for changing coordinate systems include rotations and dilations. Other types of transformations include identity transformations, orthogonal projections, oblique projections, changes to other coordinate systems, and changes of scale. In addition, other coordinate systems include polar coordinate systems, barycentric coordinate systems, and similar types of coordinate systems. Changes of scale include log scale or any other function of scale. In one embodiment, transformation 410 includes a step of converting 412 the coordinate system of the signals to modified polar coordinates, polar angle φ and polar radius R.

After conditioning 310, the conditioned state measurements for foot portion 18 undergo a transformation 410 step. Transformation 410 is performed on angle $\theta_f$ conditioned state measurement 322 and angular velocity $\dot{\theta}_f'$ conditioned state measurement 372. In one embodiment, transformation 410 includes a function shown in equation (11).

$$\beta = e^{-e^{\sqrt{\theta_f^2 + \theta_f'^2}}} \quad (11)$$

In another embodiment, transformation 410 includes a function shown in equation (12).

$$\beta = c_1 e^{-e^{\sqrt{c_2 \theta_f^2 + c_3 \theta_f'^2}}} \quad (12)$$

Where:
$c_1$=a first constant
$c_2$=a second constant
$c_3$=a third constant Transformation 410 using equation (11) or (12) produces a value β which is used in the step of converting 412 angle $\theta_s$ conditioned state measurement 320 and angular velocity $\dot{\theta}_s'$ conditioned state measurement 370 to modified polar coordinates. The values of first constant $c_1$, second constant $c_2$, and third constant $c_3$ are changed to change the value of β according to the gait device being controlled by control system 50. Angle $\theta_s$ conditioned state measurement 320, angular velocity $\dot{\theta}_s'$ conditioned state measurement 370, and β are used to convert conditioned state measurement 320 and 370 into polar coordinates. In an alternative embodiment, angle $\theta_f$ and angular velocity $\dot{\theta}_f'$ are averaged directly into a phase plot used for converting 412 to modified polar coordinates.

Figure 17:
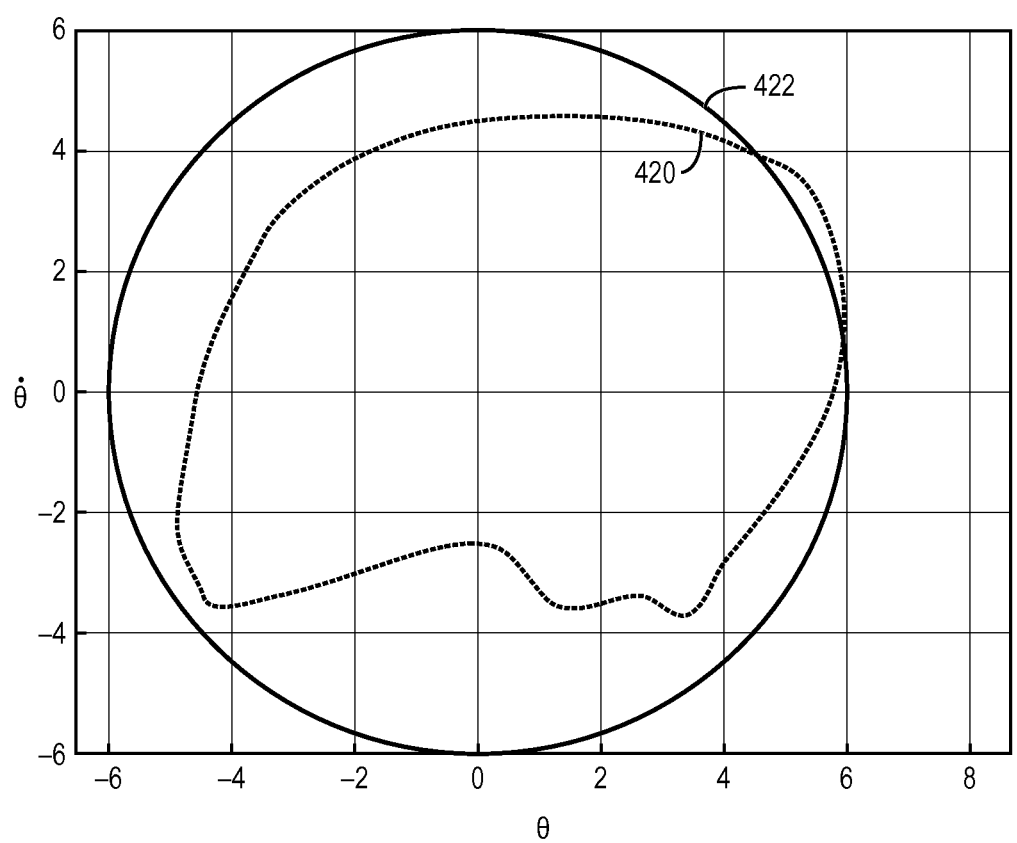
FIG. 17 illustrates a phase plot of angle and angular velocity using shank sensor data.

FIG. 17 illustrates a phase plot for angle and angular velocity using shank sensor data. The phase plot shows the change in angle $\theta_s$ and angular velocity $\dot{\theta}_s$ for shank portion 16 as user 10 walks through a gait cycle at 3 miles per hour (mph). Line 420 represents a full gait cycle, after conditioning 310 the signals from rate gyro 130 disposed on shank portion 16 and rate gyro 130 disposed on foot portion 18. In one embodiment, the y-axis of the phase plot is given by equation (13) and the x-axis of the phase plot is given by equation (14). Equation (13) uses β from equation (11) or (12).

$$Y(\dot{\theta}_s') = c_5 \dot{\theta}_s' + c_6 \dot{\theta}_s' + \beta \quad (13)$$

Where: $c_5$=a fifth constant
$c_6$=a sixth constant $$X(\theta_s) = c_7 \theta_s \quad (14)$$

Where: $c_7$=a seventh constant

Plotting $Y(\dot{\theta}_s')$ and $X(\theta_s)$ using equations (13) and (14) mitigates the bunching of signals near the origin. The use of p to convert the state measurements to modified polar coordinates also eliminates the need to use a shifting constant as described with respect to FIG. 10. Line 422 in FIG. 17 shows the phase plot of angle $\theta_f$ conditioned state measurement 322 and angular velocity $\dot{\theta}_f'$ conditioned state measurement 372 of foot portion 18.

Figure 18:
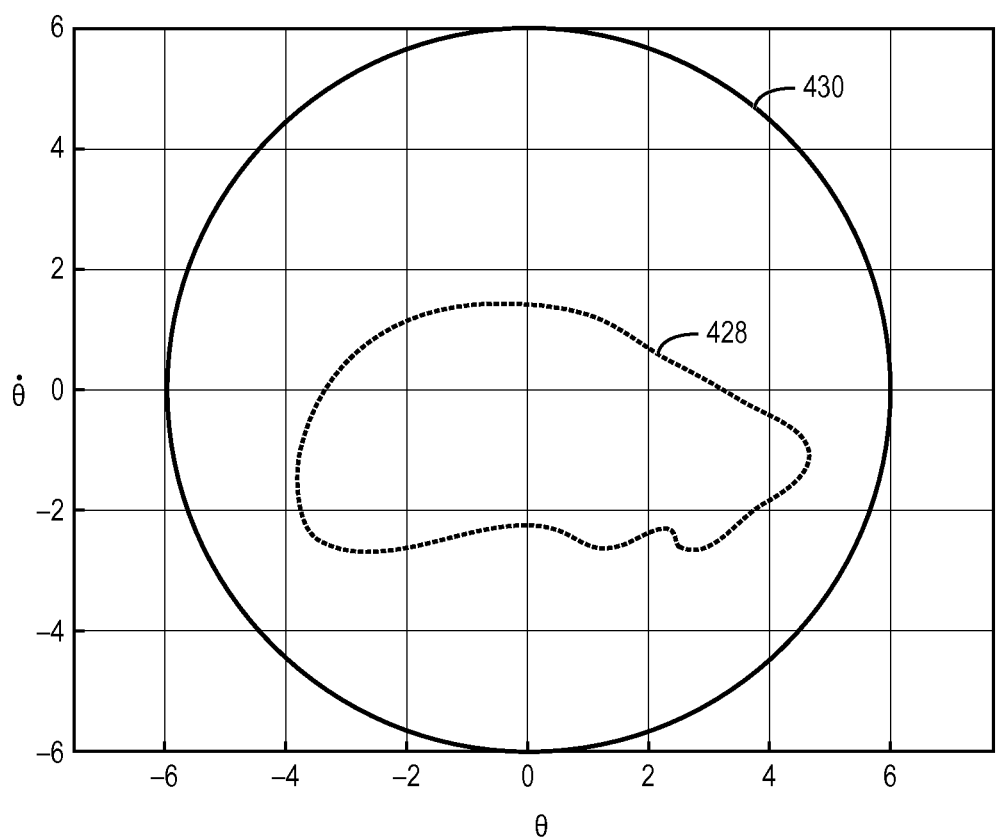
FIG. 18 illustrates a phase plot of angle and angular velocity using shank and foot sensor data.

FIG. 18 illustrates a phase plot for angle and angular velocity using shank and foot sensor data. The phase plot shows the change in angle $\theta_s$ and angular velocity $\dot{\theta}_s$ for shank portion 16 as user 10 walks through a gait cycle at 1 mph. Line 428 represents a full gait cycle, after conditioning 310 the signals from rate gyro 130 disposed on shank portion 16 and rate gyro 130 disposed on foot portion 18. Line 430 shows the phase plot of angle $\theta_f$ conditioned state measurement 322 and angular velocity $\dot{\theta}_f'$ conditioned state measurement 372 of foot portion 18.

Figure 19:
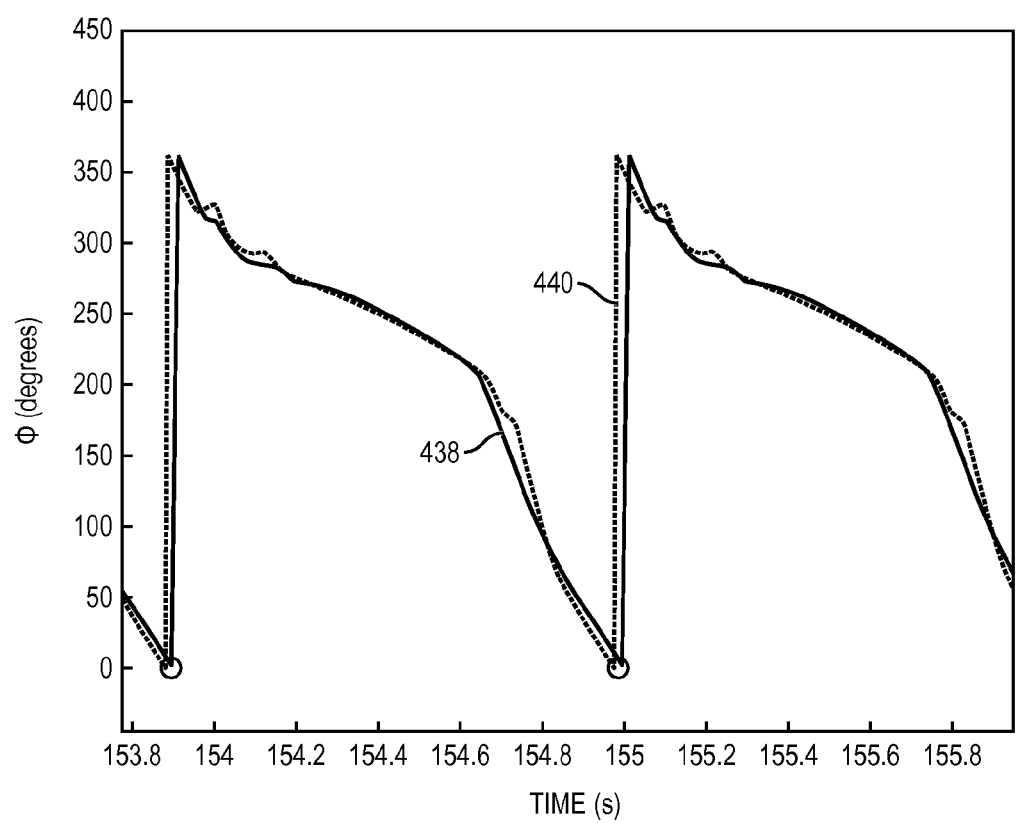
FIG. 19 illustrates a plot comparing the polar angle for a control system using shank sensor data and foot sensor data.

FIG. 19 illustrates a plot comparing the polar angle for a control system using shank sensor data and foot sensor data. Time is plotted on an x-axis and polar angle φ is plotted on a y-axis. Line 438 represents polar angle φ of the shank portion 16, and line 440 represents polar angle φ of the shank portion 16 and the foot portion 18. The noise in the output, polar angle φ, is reduced by the conditioning 310 and transformation 410 steps. The plot of polar angle φ gives additional information about user 10 stage in the gait cycle. Because the measured signal and output are related by a continuous function, the output is smooth. The measured signal is phase locked to the user's gait, and thus, the output of control system 50 is phase locked to the user's gait rather than being time based. Because control system 50 is not time-based, control system 50 better adapts to changes in gait.

Returning again to FIG. 14, polar angle φ and polar radius R are used as arguments for reference function 450 for actuator 40. Gait percent or gait progression indicates what stage user 10 is in the gait cycle and is related to the polar angle φ of the phase plot by a function of polar angle φ as shown generally in equation (3). Stride length SL and gait percent are related to polar radius R as shown generally in equation (4). Stride length SL is determined as a function of both gait percent and polar radius R. Gait percent and stride length SL from equations (3) and (4) are used as arguments in reference function 450.

Reference function 450 is based on able bodied data and is produced to match data from one or more gait activities. Such activities include walking, running, traversing slopes or stairs, avoiding obstacles, and other similar activities. An actuator position $X_a$ is predetermined for each stride length SL and gait percent through collection of able-bodied gait data and calculation of geometry for ankle prosthesis 14 to determine how actuator 40 should move. Based on stride length SL and gait percent, control system 50 looks up the desired actuator position $X_a$ and generates reference command 452 to control the position of actuator 40 to match able-bodied gait data.

Control system 50 is a continuous function relating the position of actuator 40 to a measured signal. The continuous nature of control system 50 eliminates decision making by the system, if-then logic, and changes in state. An invariant signal is used to control the gait device. By measuring kinematic or leading states, control system 50 adapts to changes in gait. Control system 50 continuously calculates an output, rather than waiting on a gait event to trigger an output. Because the measured signal and output are related by a continuous function, the output is smooth. The measured signal is phase locked to the user's gait, and thus, the output of control system 50 is phase locked to the user's gait rather than being time based. Because control system 50 is not time-based, control system better adapts to changes in gait.

Figure 20:
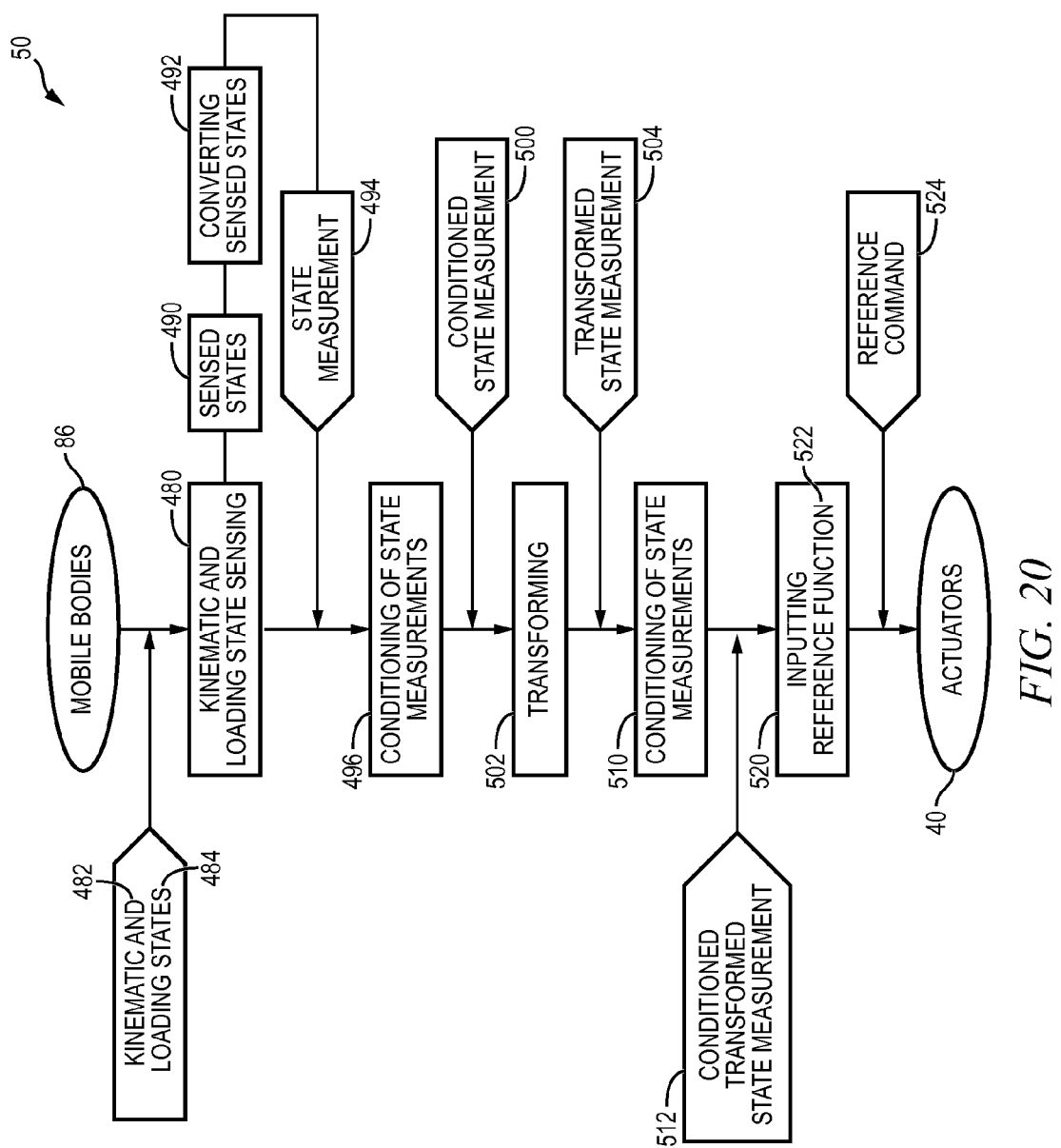
FIG. 20 illustrates a block diagram showing another method for controlling gait devices using a control system.

FIG. 20 illustrates a block diagram showing another method for controlling gait devices using control system. The method of controlling gait devices in FIG. 20 includes an additional conditioning step after the transforming step. The method for controlling gait devices using control system 50 includes the steps of sensing 480 kinematic states 482 and or loading states 484 generated by mobile bodies 86, converting 492 the sensed states 490 into state measurements 494, conditioning 496 state measurements 494 to yield conditioned state measurements 500, transforming 502 the conditioned state measurements 500 into transformed state measurements 504, conditioning 510 transformed state measurements 504 to yield conditioned transformed state measurements 512, and inputting 520 conditioned transformed state measurements 512 into a reference function 522 to derive a reference command 524.

During sensing 480, sensor 20 detects or measures one or more kinematic states 482, loading states 484, or both kinematic states 482 and loading states 484 of one or more mobile bodies 86. Kinematic state 482 and loading state 484 comprise physical states of mobile body 86. After being sensed by sensor 20, kinematic state 482 and loading state 484 comprise sensed states 490. The sensed state or sensed states 490 of mobile body 86 are processed by control system 50. After sensing of the kinematic states 482 or loading states 484 by sensors or sensor system 20, converting 492 of sensed states 490 is performed by control system 50. Sensed states 490 are converted from an output of the sensor 20 to a desired unit of measurement that yields a state measurement 494. In one embodiment, the step of converting 492 is performed by a processor of control system 50.

State measurements 494 are then conditioned 496 using control system 50 to yield conditioned state measurements 500. Conditioning 496 is realized by any filtering method, including, but not limited to Kalman filtering, transfer function use, integration, differentiation, and amplification. The filtering methods are performed as many times as desired. In one embodiment, conditioning 496 includes amplification. Amplification may result from a gain of any nonzero number, including by a unity gain. In addition, conditioning 496 may also be realized by any combination and order of filtering, integration, differentiation, and amplification. Filtering is employed for multiple uses including reduction of noise in state measurements 494, reduction of inaccuracies in state measurements 494, or alteration of state measurements 494. For example, alteration of state measurements 494 are performed in a manner similar to integration or differentiation such that drift in numerical integration or noise in numerical differentiation is eliminated.

Conditioned state measurements 500 are transformed 502 using control system 50 to yield transformed state measurements 504. The step of transforming 502 conditioned state measurements 500 is generally described as changing coordinate systems to yield transformed state measurements 504. Transformations for changing coordinate systems include isometric transformations, non-isometric transformations, rotations, and dilations. Other types of transformations include identity transformations, orthogonal projections, oblique projections, changes to other coordinate systems, and changes of scale. In addition, other coordinate systems include polar coordinate systems, barycentric coordinate systems, and similar types of coordinate systems. Changes of scale include log scale or any other function of scale. Moreover, transformations may include any transformation where the transformed state measurements are any mathematical function of the conditioned state measurements, or any combination in any order of transformations, projections, changes of coordinate system, changes of scale, or other mathematical function.

Transformed state measurements 504 are conditioned in another conditioning 510 step to obtain conditioned transformed state measurements 512. Conditioning 510 is realized by any filtering method, including, but not limited to Kalman filtering, transfer function use, integration, differentiation, and amplification.

Conditioned state measurements 500, transformed state measurements 504, and conditioned transformed state measurements 512 are used as arguments for one or more predetermined reference functions 522. The conditioned and transformed state measurements 500, 504, and 512 are used to calculate the desired reference commands 524. Each reference function 522 is a function that relates transformed state measurements 504 and conditioned transformed state measurements 512 as independent variables to the desired reference command 524 as a dependent variable. Reference function 522 is made to match data from any combination of two or more gait activities such as walking, running, traversing slopes or stairs, obstacle avoidance, or similar activities. Reference function 522 yields reference command 524, which controls the output position for actuator 40 of ankle prosthesis 12. In one embodiment, reference command 524 controls actuator 40 to match able-bodied gait data from reference function 522.

Control system 50 for gait devices, such as lower leg prosthesis 12, has several benefits. For example, the continuous nature of the reference command 524 calculation is beneficial because the method continuously measures a limb segment or robot segment directly and computes reference command 524 from a continuous differentiable function. As a result, reference command 524 is less likely to make sudden jumps or undesirable oscillations. Moreover, because reference command 524 is a function of measured quantities, generally there is no decision making and no state machine switching of states. Dealing with decision making and state transitions is known to be error prone, often resulting in undesirable operation when a state is chosen incorrectly.

Figure 21:
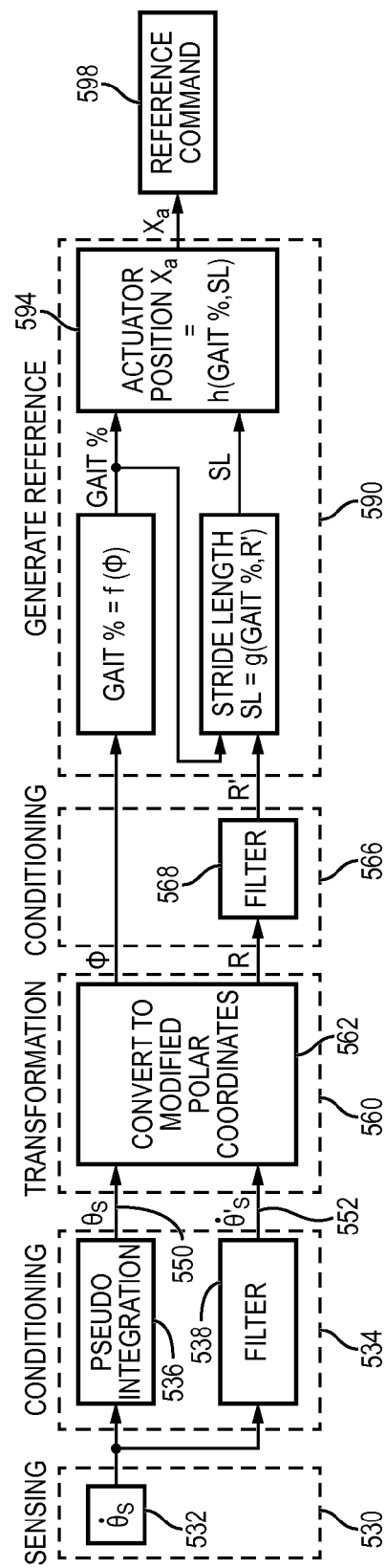
FIG. 21 illustrates a block diagram showing further detail of a method for controlling gait devices using a control system.

FIG. 21 shows a block diagram showing further detail of a method for controlling gait devices using control system 50 to control actuator 40 of ankle prosthesis 14. One or more sensors are disposed on user 10 to measure one or more kinematic states of user 10. A rate gyro 130 is disposed on shank portion 16 for sensing 530. Rate gyro 130 measures the angular velocity $\dot{\theta}_s$ kinematic state of shank portion 16 and produces angular velocity $\dot{\theta}_s$ state measurement 532 of shank portion 16. State measurement 532 is conditioned by control system 50. Conditioning 534 of angular velocity $\dot{\theta}_s$ state measurement 532 is realized by pseudo integration 536 and filtering 538. The step of pseudo integration 536 results in an angle $\theta_s$ conditioned state measurement 550.

Conditioning 534 further includes the step of filtering 538 angular velocity $\dot{\theta}_s$ state measurement 532. Filtering 538 of angular velocity $\dot{\theta}_s$ state measurement 532 results in an angular velocity $\dot{\theta}_s'$ conditioned state measurement 552. In one embodiment, filtering 538 includes a first order filter used to eliminate noise in the signal from rate gyro 130. In another embodiment, conditioning 534 is realized by any filtering method, including, but not limited to Kalman filtering, transfer function use, integration, differentiation, amplification, and any combination of the filtering methods. Filtering 538 is performed as many times as desired. Filtering 538 is employed for multiple uses including reduction of noise, reduction of inaccuracies, or alteration of angular velocity $\dot{\theta}_s$ state measurement 532.

Transformation 560 is performed on angle $\theta_s$ conditioned state measurement 550 and angular velocity $\dot{\theta}_s'$ conditioned state measurement 552. Transformation 560 includes changing coordinate system, such as by isometric, non-isometric transformations, rotations, dilations, or other suitable method. Other types of transformations include identity transformations, orthogonal projections, oblique projections, changes to other coordinate systems, and changes of scale. In addition, other coordinate systems include polar coordinate systems, barycentric coordinate systems, and similar types of coordinate systems. Changes of scale include log scale or any other function of scale. In one embodiment, transformation 560 includes a step of converting 562 the coordinate system of the signals to modified polar coordinates, polar angle φ and polar radius R.

Figure 22:
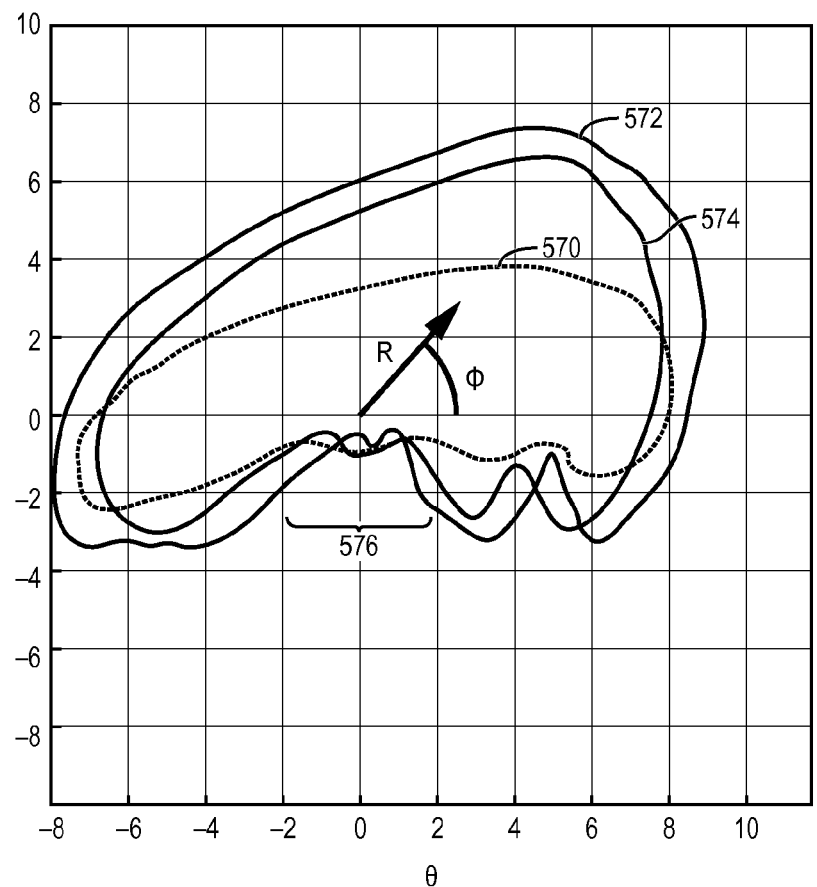
FIG. 22 illustrates a phase plot of angle and angular velocity using shank sensor data.

FIG. 22 shows a phase plot for angle and angular velocity using shank sensor data. Angle $\theta_s$ conditioned state measurement 550 is depicted as angle θ in the phase plot, and angle θ is plotted on the x-axis in rectangular coordinates. Angular velocity $\dot{\theta}_s'$ conditioned state measurement 552 is depicted as angular velocity $\dot{\theta}$ in the phase plot, and angular velocity $\dot{\theta}$ is plotted on the y-axis. The plot shows changes in angle θ and angular velocity $\dot{\theta}$ for shank portion 16 as user 10 walks through a gait cycle. The plot shows full gait cycles for user 10 walking at various speeds, where each line 570, 572, and 574 represents a different speed of gait. For example, line 570 represents a gait cycle for a slower walking speed than lines 572 and 574. Each line 570, 572, and 574 represents a full gait cycle. Region 576 shows how the signals overlap during stance phase. The phase plot shows the polar coordinates, polar angle φ and polar radius R, for gait cycles of user 10. Polar angle φ and polar radius R are calculated from angular velocity $\dot{\theta}$ and angle θ of shank portion 16.

Returning to FIG. 21, after the step of transformation 560, polar radius R undergoes conditioning 566 to obtain a conditioned polar radius R'. In one embodiment, conditioning 566 includes a filtering 568 step using equation (15).

$$R' = 10/(s+10) \quad (15)$$

The filter shown in equation (15) is a first order filter with a cutoff frequency of 10 radians/sec. Filter 568 eliminates noise and dampens oscillations in polar radius R so that different speeds, rather than overlapping, are differentiated, as shown in FIG. 23.

Figure 23:
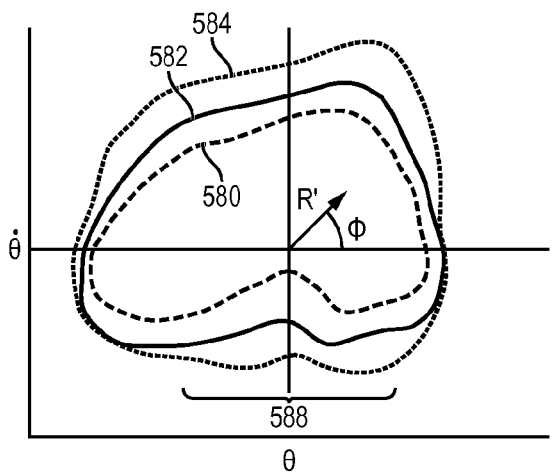
FIG. 23 illustrates a phase plot of angle and angular velocity using shank sensor data after filtering the polar radius.

FIG. 23 shows a phase plot for angle and angular velocity after filtering the polar radius R. Line 580 shows the phase plot for a slow gait speed. Line 582 shows the phase plot for an average gait speed. Line 584 shows the phase plot for a fast gait speed, relative to lines 580 and 582.

The phase plot before the filtering 568 step shows that during stance phase for different walking speeds, the phase plots converge and bunch on top of one another, as shown by region 576 in FIG. 22. After the filtering 568 step, FIG. 23 shows the phase plots for different speeds do not converge during stance phase, as shown in region 588. By filtering 568 polar radius R, the different phase plots 580, 582, and 584 are more easily differentiated. Without the filter 568, control system 50 has difficulty determining the speed of the user's gait during stance phase.

Returning again to FIG. 21, polar angle φ and conditioned polar radius R' are used as arguments for reference functions for actuator 40. One or more reference functions are used in generating 590 a reference command 598. Gait percent or gait progression indicates what stage user 10 is in the gait cycle and is related to the polar angle φ of the phase plot by a function of polar angle φ as shown generally in equation (3). Stride length SL and gait percent are related to conditioned polar radius R' as shown generally in equation (16).

$$SL = g(\text{gait \%}, R') \quad (16)$$

Stride length SL is determined as a function of both gait percent and conditioned polar radius R'. Gait percent and stride length SL from equations (3) and (16) are used as arguments in reference function 594.

Reference function 594 is based on able bodied data and is produced to match data from one or more gait activities. Such activities include walking, running, traversing slopes or stairs, avoiding obstacles, and other similar activities. An actuator position $X_a$ is predetermined for each stride length SL and gait percent through collection of able-bodied gait data and calculation of geometry for ankle prosthesis 14 to determine how actuator 40 should move. Based on stride length SL and gait percent, control system 50 looks up the desired actuator position $X_a$ and generates reference command 598 to control the position of actuator 40.

Figure 24:
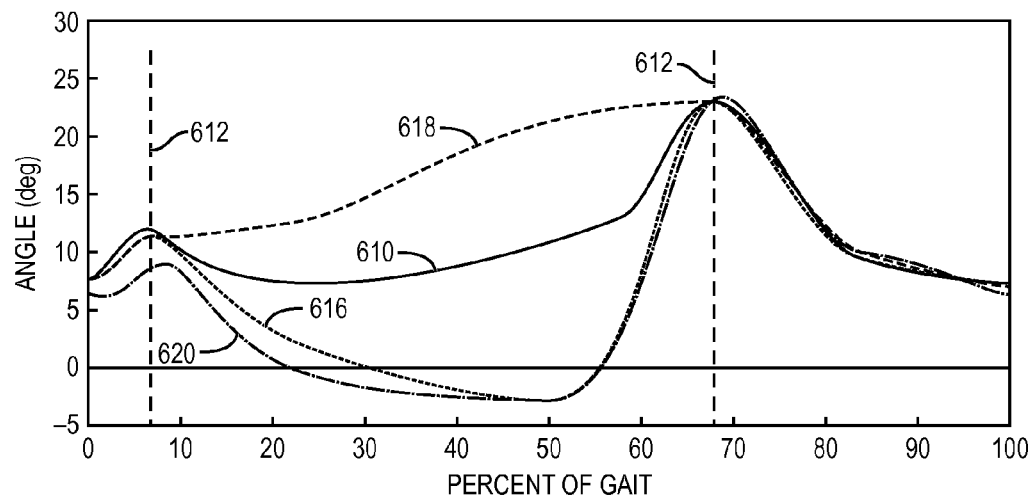
FIG. 24 illustrates an actuator trajectory and minimum jerk trajectories for an ankle actuator.

FIG. 24 shows actuator trajectories for linear stiffness and minimum jerk strategies. Minimum jerk trajectories are used to reduce current, increase battery life, reduce actuator 40 noise, and reduce acceleration of actuator 40. Jerk follows velocity $\dot{\theta}$ and acceleration $\ddot{\theta}$ as the third time derivative of position θ, by minimizing jerk, the trajectory of actuator 40 is tailored such that the trajectory maximizes smoothness, and thus eliminates unnecessary acceleration. As a result, less torque is required of actuator 40 which reduces current and increases battery life.

Consider the portion of gait between when the foot is first flat on the ground to the instant the toe leaves the ground for push off. Load is applied to the ankle by action of user 10 rolling over foot portion 18. The actuator trajectory is driven so that angle θ of the ankle prosthesis 14 matches the ankle angle data previously collected on able bodied subjects. The trajectory of actuator 40 is matched to the able bodied data by using a known linear stiffness spring and using the previously measured able bodied moment data. The trajectory of actuator 40 is shown by line 610, where ankle prosthesis 14 has a linear stiffness. The vertical boundary lines 612 mark the boundaries of the region of interest for the user's gait cycle. Between boundary lines 612 is the portion of the gait cycle beginning when foot portion 18 is first flat on the ground to the instant the toe leaves the ground for push off.

Line 616 represents the trajectory for an ankle of an able bodied subject. Line 618 represents the minimum jerk trajectory for actuator 40. Consider the ankle angle at boundary lines 612 to be necessary positions of the ankle during gait. Further, consider the trajectory of the actuator between boundary lines 612 to be freely chosen. The performance of actuator 40 benefits from choosing the least costly path between the boundary lines 612. A function that minimizes the jerk cost given a set of boundary conditions is a fifth order polynomial fitting the boundary conditions Line 620 represents the ankle angle assuming the minimum jerk actuator trajectory and no change in ankle moment from the able bodied data. Given the same applied moment from user 10, line 610 provides an output to match able bodied data, while line 618 does not. Line 620 shows the output of actuator 40 assuming minimum jerk trajectory for actuator 40 and linear stiffness. The result is that line 620 is similar to able bodied data, line 616. Any difference in line 620 and line 616 is accounted for by the user adjusting the applied moment and ankle angle.

Figure 25:
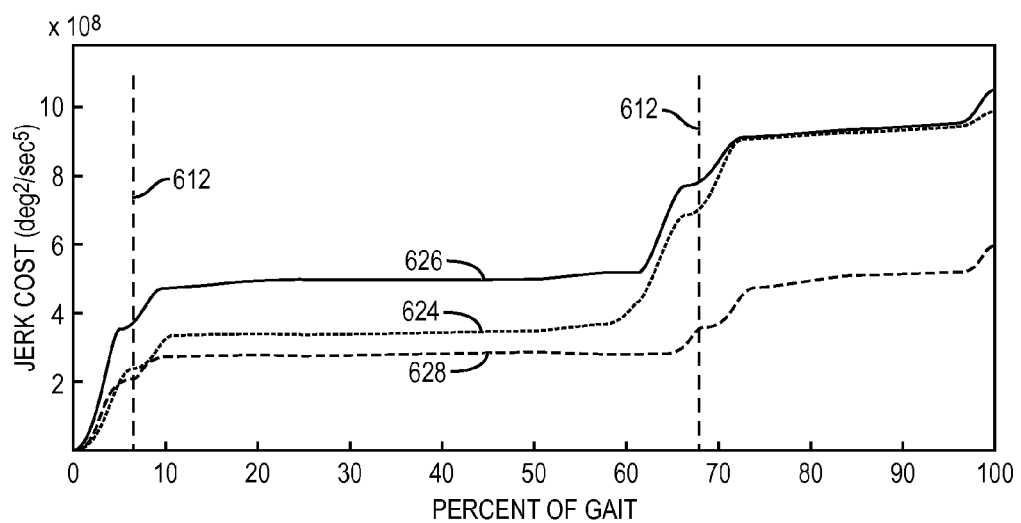
FIG. 25 illustrates the jerk cost for the minimum jerk trajectory of an ankle actuator.

FIG. 25 shows the jerk cost for the minimum jerk trajectory of an ankle actuator and the trajectory from a linear spring stiffness. The jerk cost is the integral of the square of the third derivative of position over the path is used to minimize jerk cost. Line 624 shows the jerk cost of ankle angle. Line 626 shows the path for a linear spring. Line 628 shows a minimum jerk trajectory. Between the vertical boundary lines 612, where the minimum jerk strategy is applied, line 628 shows the cumulative jerk cost is lower. Because minimum jerk strategy is applied, the acceleration required of actuator 40 is lower because the trajectory is smoother. Reduced acceleration of actuator 40 results in a reduced current needed for actuator 40. Unnecessary acceleration of actuator 40 is reduced. The reduction in current translates into longer battery life and a higher threshold for performance of actuator 40. Performance of actuator 40 is limited by the heat produced by actuator 40. Where more of the available current, which heats actuator 40 and control system 50, is used to drive the system, actuator 40 and control system 50 perform better under more demanding conditions. By using minimum jerk trajectories for the stance phase of gait, performance and battery life of actuator 40 and control system 50 is improved.

Figure 26:
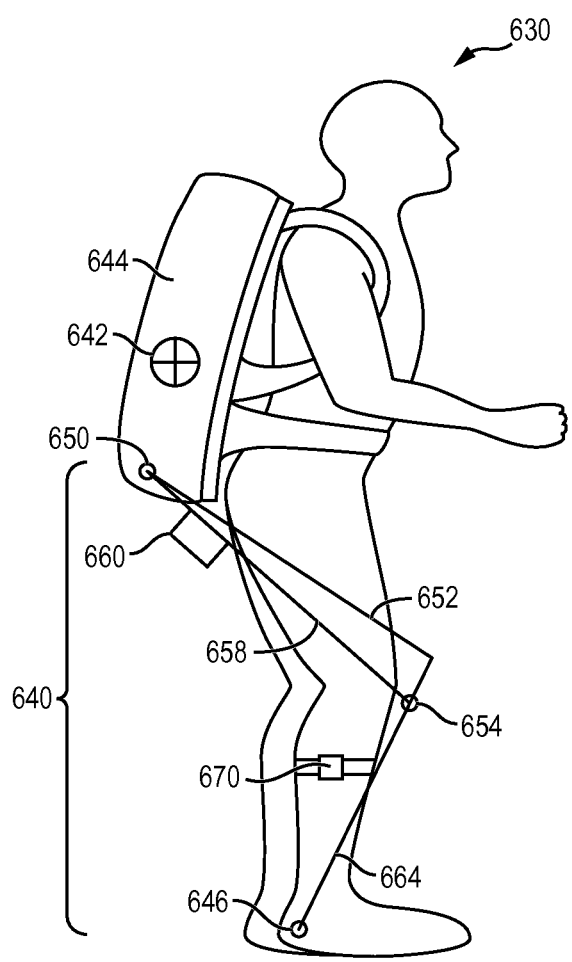
FIG. 26 illustrates a gait augmentation device with a control system.

FIG. 26 shows a representation of user 630 wearing a gait augmentation device which includes a control system for controlling the operation of the device. A gait augmentation device 640 comprises a load carrying device that transmits a load 642 from a backpack 644 to foot portion 646. Foot portion 646 couples to a shoe worn by user 630. Gait augmentation device 640 includes a load receptor point 650 coupled to backpack 644. Load receptor point 650 receives the gravitational load 642 of backpack 644. Upper arm 652 extends downward from the load receptor point 650 to a knee joint 654. Upper arm 652 acts as a stabilizing member.

An actuator arm 658 extends between load receptor point 650 and knee joint 654, generally in parallel with upper arm 652. Actuator arm 658 is a load transmitting member, including a compliant member, such as a compression spring, disposed between an actuator 660 and knee joint 654. Actuator arm 658 is adjustable to selectively open and close a gap between the compliant member and knee joint 654. Actuator arm 658 includes actuator 660 for selectively changing the effective length of the compliant member and for selectively closing or opening the gap between compliant member and knee joint 654. A leg member 664 extends downward from knee joint 654 to foot portion 646.

A sensor or sensor system 670 is worn by user 630. In one embodiment, sensor 670 is worn on the lower leg of user 10. In another embodiment, sensor 670 is disposed on ankle, thigh, foot, or other part of user 630. In yet another embodiment, a plurality of sensors 670 is disposed on user 630. Sensor 670 detects a kinematic state, a loading state, or a kinematic state and a loading state of user 630. Measurements from sensor 670 are used by control system 50 to control actuator 660 using the methods disclosed above.

When control system 50 determines that the user's foot is planted on the ground, during stance phase of gait, control system 50 engages actuator 660 to open the gap between the compliant member and knee joint 654. Load 642 is transmitted between backpack 644 and foot portion 646. When control system 50 determines that the user's foot is lifted off the ground, during swing phase of gait, control system 50 engages actuator 660 to open the gap between the compliant member and knee joint 654. Load 642 is no longer transmitted between backpack 644 and foot portion 646.

Control system 50 is a continuous function relating the position of actuator 660 to a measured signal. The continuous nature of control system 50 eliminates decision making by the system, if-then logic, and changes in state. By measuring kinematic or leading states, control system 50 adapts to changes in gait. Because user 630 moves independently of gait augmentation device 640, control system 50 senses the kinematic motion of user 630 to determine the user's intent. In one embodiment, a processor of control system 50 operates at 1000 Hz. User 630 moves without having to force gait augmentation device 640 and does not experience drag from the device.

Control system 50 continuously calculates an output, rather than waiting on a gait event to trigger an output. Because the measured signal and output are related by a continuous function, the output is smooth. The measured signal is phase locked to the user's gait, and thus, the output of control system 50 is phase locked to the user's gait rather than being time based. Because control system 50 is not time-based, control system 50 better adapts to changes in gait.

Figure 27:
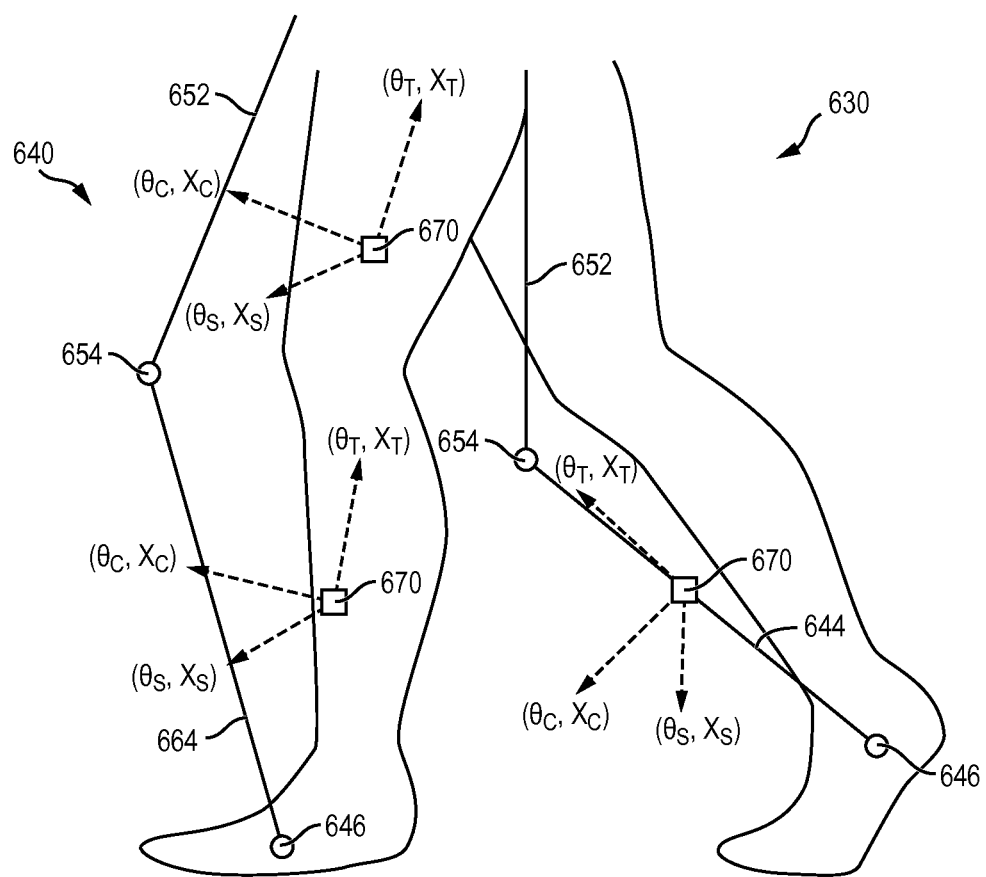
FIG. 27 illustrates a schematic representation of a gait augmentation device, showing an example of coordinate systems of kinematic states.

FIG. 27 shows a schematic representation of a gait augmentation robot and showing coordinate systems of kinematic states. Sensor 670 measures the kinematic state or loading state of a mobile body of user 630. A mobile body includes a limb segment or a robotic segment. A kinematic state includes an angular position, linear position, linear velocity, angular velocity, linear acceleration, or angular acceleration associated with a mobile body with reference to a fixed world frame or a frame fixed to any other mobile body. A loading state includes a moment or force experienced by the mobile body.

Sensors 670 are configured to measure kinematic state, such as velocities, accelerations, angular positions, and linear positions in coordinate frames, which are oriented with the limb segment or robotic segment to which sensors 670 are affixed. A limb segment includes, for example, lower leg of user 630. A robotic segment includes, for example, an upper arm 652 or leg member 664 of gait augmentation device 640. Sensor 670 determines the kinematic state of user 630 in linear coordinates, polar coordinates, or a combination of coordinate systems. The coordinate frames have three orthogonal axes: a sagittal axis ($\theta_S$, $X_S$), a coronal axis ($\theta_C$, $X_C$), and a transverse axis ($\theta_T$, $X_T$). The sagittal axis ($\theta_S$, $X_S$) is oriented normal to the sagittal plane of the mobile body, while the coronal axis ($\theta_C$, $X_C$) is oriented normal to the coronal plane of the mobile body, and the transverse axis ($\theta_T$, $X_T$) is oriented normal to the transverse plane of the mobile body. Each sensor 20 is oriented so that the axis of measurement is any linear combination of three unit vectors in the direction of the sagittal axis ($\theta_S$, $X_S$), coronal axis ($\theta_C$, $X_C$), and transverse axis ($\theta_T$, $X_T$).

Control system 50 processes the information or data from sensor 670 to produce an output signal used to control actuator 660. Control system 50 includes a processor to store and process data from sensor 670. The method for controlling gait devices includes a series of operations performed on kinematic or loading data. The operations performed by control system 50 relate kinematic motion to a desired output of actuator 660. The various methods for controlling gait augmentation device 640 are described in relation to FIGS. 5-25 above.

Figure 28:
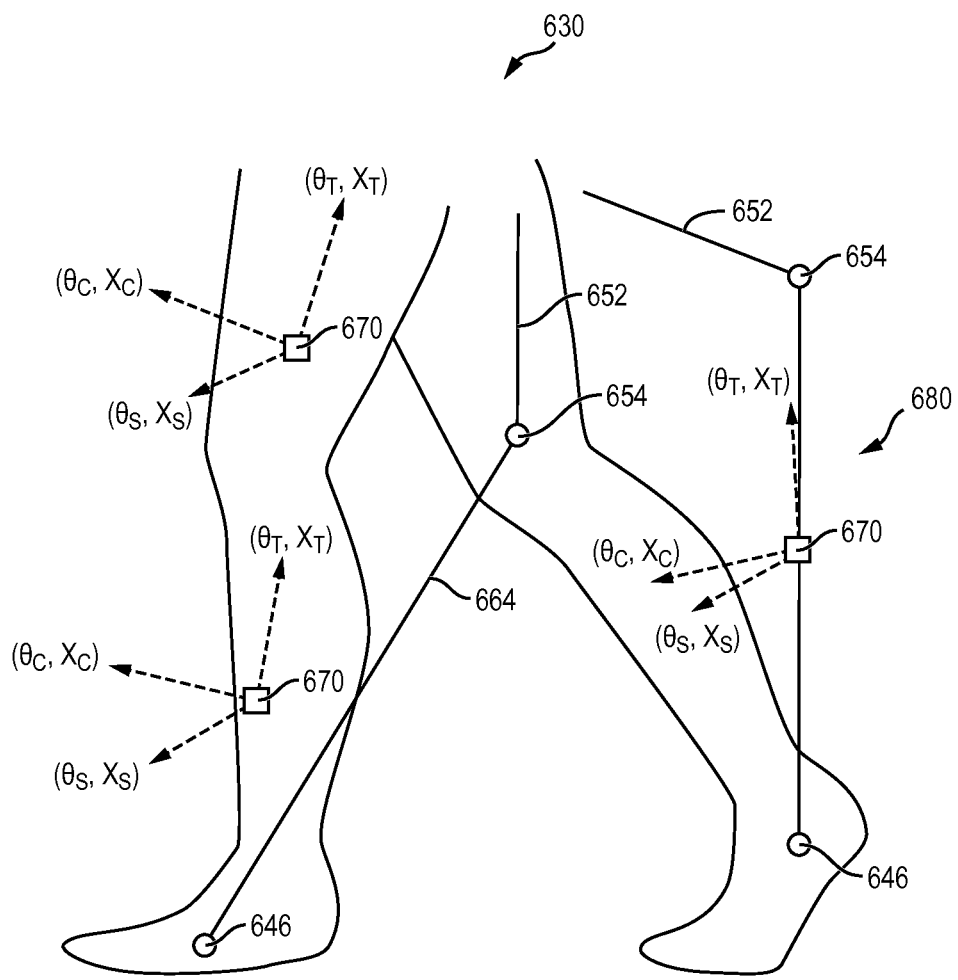
FIG. 28 illustrates a schematic representation of an alternative gait augmentation device.

FIG. 28 shows a schematic representation of an alternative gait augmentation device and showing coordinate systems of kinematic states. A gait augmentation device 680 is similar to gait augmentation device 640 comprises a load carrying device that transmits a load 642 from a backpack 644 to foot portion 646. Control system 50 is adapted to gait augmentation device 680, which includes an alternative orientation for upper arm 652, knee joint 654, and leg member 664.

Control system 50 processes the information or data from one or more sensor 670 to produce an output signal used to control actuator 660. Control system 50 includes a processor to store and process data from sensor 670. The method for controlling gait devices includes a series of operations performed on kinematic or loading data. The operations performed by control system 50 relate kinematic motion to a desired output of actuator 660. The various methods for controlling gait augmentation device 680 are described in relation to FIGS. 5-25 above.

Therefore, control systems and methods for controlling gait devices are disclosed. The control systems and methods may be employed in a wide field of applications. Some examples, which are in no way exhaustive, include controlling lower limb prostheses and orthotic devices and assisting in the operation of exoskeleton devices. Also, the method may be employed in computer animation, gaming, and other fields where the control of robotic and bionic machines benefit from characterization of cyclic patterns.

While one or more embodiments of the present invention have been illustrated in detail, the skilled artisan will appreciate that modifications and adaptations to those embodiments may be made without departing from the scope of the present invention as set forth in the following claims.

What is claimed is:

1. A method of controlling a user mobility assistance device, comprising:
   measuring a physical state of a mobile body of the user mobility assistance device or the user;
   transforming the physical state of the mobile body into a measured attribute of the mobile body;
   implementing a reference function based on a reference user's mobility, wherein the reference function includes a three dimensional (3D) surface that correlates attributes of the reference user's mobility;
   applying the measured attribute of the mobile body to the reference function to generate a reference command by determining a position on the 3D surface based on the measured attribute of the mobile body to control the user mobility assistance device.

2. The method of claim 1, wherein transforming the physical state involves changing to a coordinate system for the measured attribute of the mobile body having a different number of dimensions than the physical state.

3. The method of claim 1, wherein transforming the physical state includes changing to a coordinate system of measured attributes of stride length and gait percent.

4. The method of claim 1, wherein the measured attribute of the mobile body includes stride length or gait percent.

5. The method of claim 1, wherein implementing the reference function includes:
   measuring a physical state of an able-bodied human;
   transforming the physical state of the able-bodied human into the attributes of reference user mobility; and
   generating the surface representing operation of the user mobility assistance device with the attributes of reference user mobility.

6. The method of claim 1, wherein the reference command maintains a continuous output from the surface phase locked to the measured attribute of the mobile body.

7. A method of controlling a user mobility assistance device, comprising:
   measuring a physical state of a mobile body of the user mobility assistance device or the user to obtain a physical state measurement;
   transforming the physical state measurement into a measured attribute of the mobile body;
   implementing a reference function based on a reference user's mobility, wherein the reference function includes a three dimensional (3D) surface correlating attributes of reference user's mobility; and
   applying the measured attribute of the mobile body to the reference function to generate a reference command by determining a position on the 3D surface based on the measured attribute of the mobile body to control the user mobility assistance device.

8. The method of claim 7, further including conditioning the physical state measurement prior to applying the measured attribute of the mobile body to the reference function.

9. The method of claim 7, wherein the mobile body includes a limb of a user or a robotic device.

10. The method of claim 7, wherein providing the reference function includes:
    measuring a physical state of an able-bodied human;
    transforming the physical state of the able-bodied human into the attributes of reference user mobility; and
    generating the 3D surface representing operation of the user mobility assistance device with the attributes of reference user mobility.

11. The method of claim 10, further including actuating an actuator to control the user mobility assistance in response to the reference command.

12. The method of claim 7, wherein transforming the physical state measurement involves changing to a coordinate system for the measured attribute of the mobile body having a different number of dimensions than the physical state measurement.

13. The method of claim 7, wherein the measured attribute of gait activity include stride length or gait percent.

14. A method of controlling a gait device, comprising:
    sensing a physical state of a mobile body of the gait device or a user of the gait device in response to gait activity to obtain a physical state measurement;
    conditioning the physical state measurement to provide a conditioned state measurement;
    transforming the conditioned state measurement into a measured attribute of the gait activity;
    implementing a reference function based on an able-bodied gait activity, wherein the reference function includes a three dimensional (3D) surface correlating attributes of the able-bodied gait activity;
    applying the measured attribute of gait activity to the reference function to generate a reference command by determining a position on the 3D surface based on the measured attribute of gait activity; and
    controlling the gait device with the reference command.

15. The method of claim 14, wherein providing the reference function includes:
    measuring a physical state of an able-bodied human;
    transforming the physical state of the able-bodied human into the attributes of able-bodied gait activity; and
    generating the 3D surface representing operation of the gait device with the attributes of able-bodied gait activity.

16. The method of claim 15, further including controlling the gait device by moving an actuator in response to the reference command.

17. The method of claim 14, wherein transforming the conditioned state measurement involves changing to a coordinate system for the measured attribute of gait activity having a different number of dimensions than the conditioned state measurement.

18. The method of claim 14, wherein transforming the conditioned state measurement includes changing to a coordinate system of measured attributes of stride length and gait percent.

19. The method of claim 14, wherein the measured attribute of gait activity include stride length or gait percent.

20. The method of claim 14, wherein the reference command maintains a continuous output from the 3D surface phase locked to the measured attribute of gait activity.

21. A method of controlling a gait device using a control system within the gait device, comprising:
    disposing a first sensor on a first mobile body of the gait device or a user of the gait device;

measuring a physical state of the first mobile body in response to a gait activity using the first sensor to obtain a first physical state measurement of the gait activity;

disposing a second sensor on a second mobile body;

measuring a physical state of the second mobile body in response to the gait activity using the second sensor to obtain a second physical state measurement of the gait activity;

conditioning the first physical state measurement and second physical state measurement to provide a first conditioned state measurement and a second conditioned state measurement;

transforming the first conditioned state measurement and second conditioned state measurement by changing to a coordinate system of measured attributes of stride length and gait percent;

implementing a reference function within the control system based on a normal gait activity, wherein the reference function is a three dimensional (3D) surface correlating attributes of normal gait activity;

applying the measured attributes of stride length and gait percent to the reference function to generate a reference command by determining a position on the 3D surface from the measured attributes of stride length and gait percent, wherein the reference command maintains a continuous output from the 3D surface phase locked to the measured attributes of stride length and gait percent; and controlling the gait device with the reference command.

22. The method of claim 21, further including converting units of measure of the first physical state measurement and second physical state measurement.

23. The method of claim 21, wherein measuring the physical state of the first mobile body includes measuring a kinematic state or loading state of the first mobile body.

24. The method of claim 21, wherein implementing the reference function includes:

measuring a physical state of an able-bodied human;

transforming the physical state of the able-bodied human into the attributes of normal gait activity; and generating the 3D surface representing operation of the gait device with the attributes of normal gait activity.

25. The method of claim 24, further including controlling the gait device by moving an actuator in response to the reference command.

* * * * *